(12) United States Patent
Brannan

(10) Patent No.: US 9,668,802 B2
(45) Date of Patent: Jun. 6, 2017

(54) DEVICES AND METHODS FOR OPTICAL DETECTION OF TISSUE CONTACT

(71) Applicant: COVIDIEN LP, Mansfield, MA (US)

(72) Inventor: Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 328 days.

(21) Appl. No.: 14/017,995

(22) Filed: Sep. 4, 2013

(65) Prior Publication Data

US 2014/0094789 A1  Apr. 3, 2014

Related U.S. Application Data

(60) Provisional application No. 61/708,922, filed on Oct. 2, 2012.

(51) Int. Cl.
*A61B 18/12* (2006.01)
*A61B 18/18* (2006.01)
(Continued)

(52) U.S. Cl.
CPC ...... *A61B 18/1233* (2013.01); *A61B 18/1815* (2013.01); *A61B 2017/00057* (2013.01);
(Continued)

(58) Field of Classification Search
CPC ............ A61B 18/1233; A61B 18/1815; A61B 2018/00708; A61B 2019/465; A61B 2017/00057
(Continued)

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 | 6/1995 |
| DE | 390937 | 3/1924 |

(Continued)

OTHER PUBLICATIONS

U.S. Appl. No. 13/419,981, filed Mar. 14, 2012, Joseph D. Brannan.
(Continued)

*Primary Examiner* — Thomas Giuliani

(57) ABSTRACT

An electrosurgical system includes an energy applicator adapted to direct energy to tissue, an electrosurgical power generating source, and a surface-contact detection device. The surface-contact detection device is operably associated with the energy applicator. The surface-contact detection device is communicatively-coupled to the electrosurgical power generating source. The surface-contact detection device includes at least one optical transmitter to generate optical signals, a lens member configured to reflect optical signals generated by the optical transmitter when the lens member is disposed in contact with tissue, and at least one optical receiver to receive optical signals reflected by the lens member. The electrosurgical power generating source is adapted to transmit energy to the energy applicator when it is determined that the lens member is disposed in contact with tissue.

20 Claims, 16 Drawing Sheets

(51) Int. Cl.
  *A61B 18/00* (2006.01)
  *A61B 17/00* (2006.01)
  *A61B 90/00* (2016.01)
(52) U.S. Cl.
  CPC ............ *A61B 2018/00708* (2013.01); *A61B 2018/00761* (2013.01); *A61B 2018/00785* (2013.01); *A61B 2090/065* (2016.02)
(58) Field of Classification Search
  USPC .............................................. 606/33, 34, 41
  See application file for complete search history.

(56) References Cited

U.S. PATENT DOCUMENTS

| | | |
|---|---|---|
| D266,842 S | 11/1982 | Villers et al. |
| D278,306 S | 4/1985 | McIntosh |
| 4,557,272 A | 12/1985 | Carr |
| 4,612,940 A | 9/1986 | Kasevich et al. |
| D295,893 S | 5/1988 | Sharkany et al. |
| D295,894 S | 5/1988 | Sharkany et al. |
| 5,334,183 A | 8/1994 | Wuchinich |
| D354,218 S | 1/1995 | Van de Peer |
| 5,558,672 A | 9/1996 | Edwards et al. |
| 5,588,432 A | 12/1996 | Crowley |
| 5,762,609 A | 6/1998 | Benaron et al. |
| 5,893,848 A | 4/1999 | Negus et al. |
| 5,919,219 A | 7/1999 | Knowlton |
| D424,693 S | 5/2000 | Pruter |
| D424,694 S | 5/2000 | Tetzlaff et al. |
| D425,201 S | 5/2000 | Tetzlaff et al. |
| 6,283,961 B1 | 9/2001 | Underwood et al. |
| D449,886 S | 10/2001 | Tetzlaff et al. |
| D457,958 S | 5/2002 | Dycus et al. |
| D457,959 S | 5/2002 | Tetzlaff et al. |
| 6,461,352 B2 | 10/2002 | Morgan et al. |
| 6,492,957 B2 | 12/2002 | Carillo, Jr. et al. |
| 6,514,249 B1 | 2/2003 | Maguire et al. |
| 6,623,423 B2 | 9/2003 | Sakurai et al. |
| D487,039 S | 2/2004 | Webster et al. |
| D496,997 S | 10/2004 | Dycus et al. |
| D499,181 S | 11/2004 | Dycus et al. |
| 7,041,095 B2 | 5/2006 | Wang et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| 7,241,293 B2 | 7/2007 | Davison |
| 7,270,658 B2 | 9/2007 | Woloszko et al. |
| 7,278,991 B2 | 10/2007 | Morris et al. |
| 7,306,592 B2 | 12/2007 | Morgan et al. |
| D564,662 S | 3/2008 | Moses et al. |
| D576,932 S | 9/2008 | Strehler |
| 7,425,212 B1 | 9/2008 | Danek et al. |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| 7,840,253 B2 | 11/2010 | Tremblay et al. |
| D634,010 S | 3/2011 | DeCarlo |
| 8,172,757 B2 | 5/2012 | Jaffe et al. |
| 8,214,010 B2 | 7/2012 | Courtney et al. |
| D681,810 S | 5/2013 | DeCarlo |
| 2002/0173781 A1* | 11/2002 | Cense ................ A61B 18/203 606/9 |
| 2004/0015159 A1 | 1/2004 | Slater et al. |
| 2005/0038419 A9 | 2/2005 | Arnold et al. |
| 2005/0222558 A1 | 10/2005 | Baxter et al. |
| 2006/0200121 A1 | 9/2006 | Mowery |
| 2007/0060819 A1* | 3/2007 | Altshuler .............. A61B 5/0059 600/475 |
| 2007/0191825 A1 | 8/2007 | Cronin et al. |
| 2007/0287998 A1 | 12/2007 | Sharareh et al. |
| 2010/0268220 A1* | 10/2010 | Johnson ................ A61B 18/18 606/33 |
| 2012/0226268 A1* | 9/2012 | Liu ...................... A61B 18/203 606/9 |
| 2014/0094797 A1* | 4/2014 | Brannan ............ A61B 18/1233 606/35 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| EP | 2314246 A1 | 4/2011 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |

(56) References Cited

FOREIGN PATENT DOCUMENTS

| JP | 09010223 | 1/1997 |
|---|---|---|
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| KR | 20070093068 | 9/2007 |
| KR | 20100014406 | 2/2010 |
| KR | 20120055063 | 5/2012 |
| SU | 166452 | 11/1964 |
| SU | 401367 | 11/1974 |
| SU | 727201 | 4/1980 |
| WO | WO90/07303 | 7/1990 |
| WO | WO97/24074 | 7/1997 |
| WO | WO00/36985 | 6/2000 |
| WO | 2004110258 A2 | 12/2004 |
| WO | 2009075879 A1 | 6/2009 |
| WO | WO2010/035831 | 4/2010 |
| WO | 2012106678 A1 | 8/2012 |

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.

(56) References Cited

OTHER PUBLICATIONS

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non•LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

(56) References Cited

OTHER PUBLICATIONS

Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology , "Overcoming the Challenge" located at: <http://www.urologix.com!medicaUtechnology.html >Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et aI., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report from Application No. EP 13186124.7 dated Jan. 17, 2014.
European Examination Report from Appl. No. EP 13 186 124.7 dated Feb. 25, 2016.
Chinese Office Action dated Aug. 2, 2016 in corresponding Chinese Patent Application No. 201310453229.6.

* cited by examiner

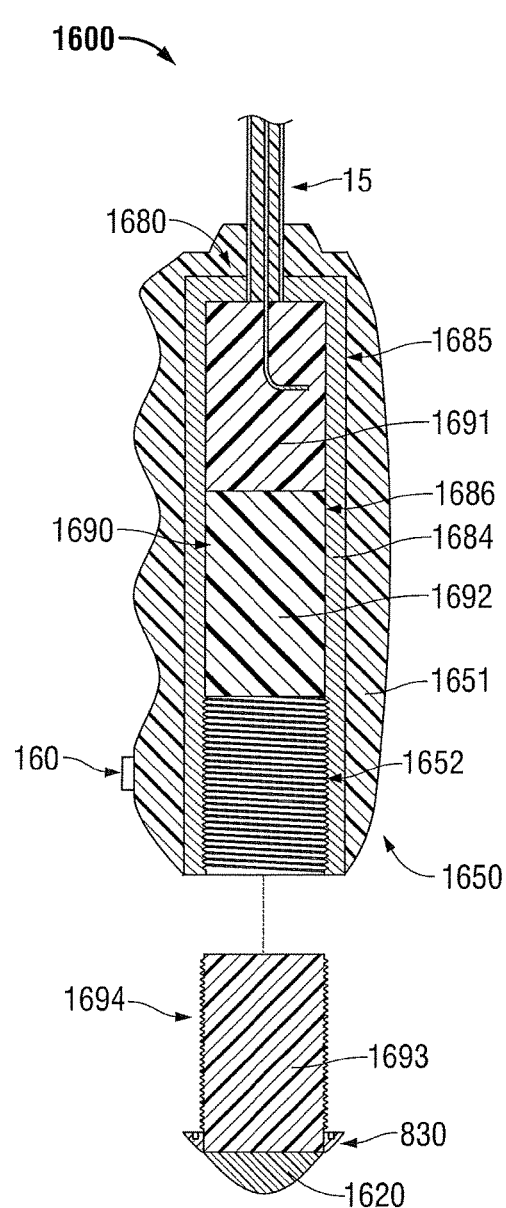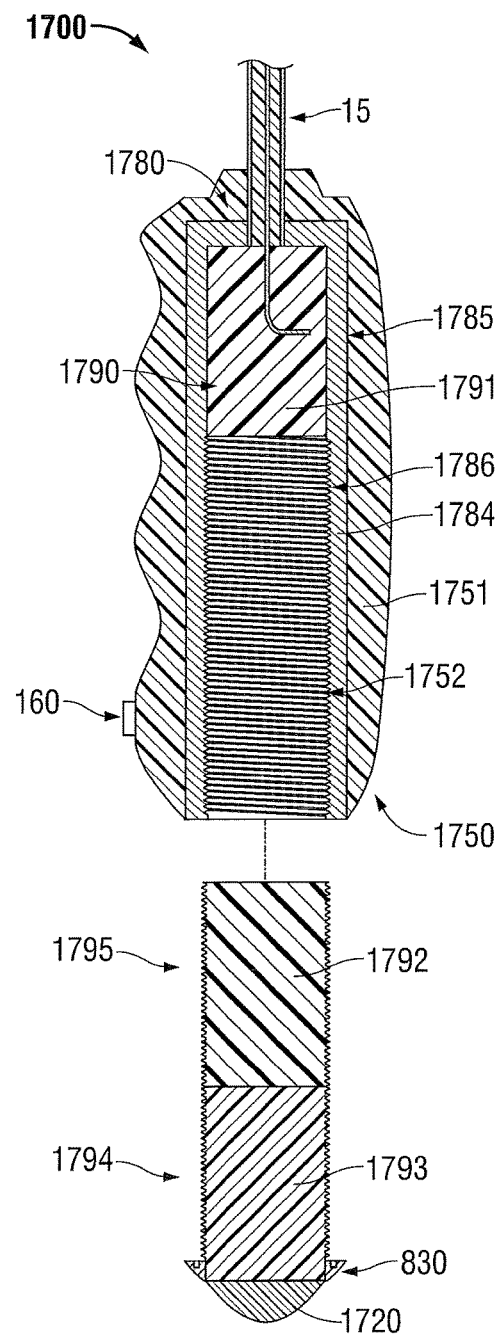
FIG. 16
FIG. 17

DEVICES AND METHODS FOR OPTICAL DETECTION OF TISSUE CONTACT

CROSS REFERENCE TO RELATED APPLICATION

The present application claims the benefit of and priority to U.S. Provisional Application Ser. No. 61/708,922, filed on Oct. 2, 2012, the entire contents of which are incorporated herein by reference.

BACKGROUND

1. Technical Field

The present disclosure relates to electrosurgical systems and devices for performing medical procedures. The present disclosure also relates to detection devices for use in connection with electrosurgical devices. More particularly, the present disclosure relates to systems, devices and methods for optical detection of surface contact of an electrosurgical device surface to tissue. The present disclosure also relates to electrosurgical devices including a waveguide with dielectric structures. The present disclosure also relates to electrosurgical devices including a waveguide with removable dielectric structures. The present disclosure also relates to methods of directing energy to tissue using the same.

2. Discussion of Related Art

Electrosurgical instruments have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using a handpiece including a surgical instrument (e.g., end effector, ablation probe, or electrode) adapted to transmit energy to a tissue site during electrosurgical procedures, an electrosurgical generator operable to output energy, and a cable assembly operatively connecting the surgical instrument to the generator.

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. A microwave transmission line typically includes a thin inner conductor that extends along the longitudinal axis of the transmission line and is surrounded by a dielectric material and is further surrounded by an outer conductor around the dielectric material such that the outer conductor also extends along the transmission line axis.

Dielectric properties of biological tissues are determining factors for the dissipation of electromagnetic energy in the body. Tissue impedance can vary widely among tissue types and can vary according to the quality and quantity of fluids surrounding the tissue. For tissue ablation purposes, there is a need to match the impedance of the microwave transmission line to the impedance of the tissue.

SUMMARY

According to an aspect of the present disclosure, an electrosurgical device is provided. The electrosurgical device includes a surface-contact detection device including a lens member, one or more optical transmitters to generate optical signals, and one or more optical receivers to receive optical signals reflected by the lens member. The lens member is adapted to allow the one or more optical transmitters and the one or more optical receivers to communicate when the lens member is disposed in contact with tissue.

According to an aspect of the present disclosure, an electrosurgical system is provided. The electrosurgical system includes an energy applicator adapted to direct energy to tissue, an electrosurgical power generating source, and a surface-contact detection device. The surface-contact detection device is operably associated with the energy applicator. The surface-contact detection device is communicatively-coupled to the electrosurgical power generating source. The surface-contact detection device includes at least one or more optical transmitters to generate optical signals, a lens member configured to reflect optical signals generated by the one or more optical transmitters when the lens member is disposed in contact with tissue, and one or more optical receivers to receive optical signals reflected by the lens member. The electrosurgical power generating source is adapted to transmit energy to the energy applicator when it is determined that the lens member is disposed in contact with tissue.

One or more operating parameters associated with the electrosurgical power generating source may be controlled based on an electrical signal received from the surface-contact detection device.

In any one of the aspects, the lens member is configured to reflect optical signals generated by the one or more optical transmitters when the lens member is disposed in contact with tissue.

According to another aspect of the present disclosure, an electrosurgical device is provided. The electrosurgical device includes an energy applicator adapted to direct energy to tissue. The energy applicator includes an antenna assembly. The antenna assembly includes a waveguide. The waveguide includes an open end and electrically-conductive walls defining a cavity therein. The cavity is disposed in communication with the open end. A first dielectric structure including a plurality of dielectric layers is disposed at least partially within the cavity. A second dielectric structure is disposed distally to the distal end of the waveguide walls and coupled to the distal end of the first dielectric structure. One or more of the dielectric layers of the first dielectric structure disposed at least partially within the cavity are adapted to be removable from the waveguide.

According to another aspect of the present disclosure, an electrosurgical system is provided. The electrosurgical system includes an energy applicator adapted to direct energy to tissue, an electrosurgical power generating source, and a surface-contact detection device operably associated with the energy applicator. The energy applicator includes an antenna assembly including a waveguide that includes an open end and electrically-conductive walls defining a cavity therein. The cavity is disposed in communication with the open end. The energy applicator further includes a dielectric structure including a plurality of dielectric layers. The dielectric structure is disposed at least partially within the cavity. The surface-contact detection device is communicatively-coupled to the electrosurgical power generating source. The surface-contact detection device includes one or more optical transmitters to generate optical signals, a lens member configured to reflect optical signals generated by the one or more optical transmitters when the lens member is disposed in contact with tissue, and one or more optical receivers to receive optical signals reflected by the lens member. The electrosurgical power generating source is adapted to transmit energy to the energy applicator based on a determination that optical signals generated by the one or more optical transmitters result in reflected optical signals received at the one or more optical receivers.

According to another aspect of the present disclosure, a method of directing energy to tissue is provided. The method includes the initial step of positioning an energy applicator for delivery of energy to target tissue. The energy applicator is provided with a surface-contact detection device including one or more optical transmitters and one or more optical receivers. The energy applicator is operably associated with an electrosurgical power generating source. The method also includes the steps of determining whether a radiating portion of the energy applicator is disposed in contact with the target tissue based on a determination of whether optical signals generated by the one or more optical transmitters result in reflected optical signals received at the one or more optical receivers, and if it is determined that the radiating portion of the energy applicator is disposed in contact with tissue, transmitting energy from the electrosurgical power generating source through the radiating portion to the target tissue.

The method may further include the step of determining whether to transmit an electrical signal indicative of an alarm condition using the surface-contact detection device. Determining whether to transmit an electrical signal indicative of an alarm condition may further include the step of monitoring whether a radiating portion of an energy applicator is disposed in contact with target tissue based on a determination of whether optical signals generated the at least one optical transmitter result in reflected optical signals received at the at least one optical receiver. Determining whether to transmit an electrical signal indicative of an alarm condition may further include the step of causing cessation of energy delivery from the electrosurgical power generating source through the radiating portion to the target tissue if it is determined that optical signals generated by the at least one optical transmitter do not result in reflected optical signals received at the at least one optical receiver.

According to another aspect of the present disclosure, a method of directing energy to tissue is provided. The method includes the initial step of positioning an energy applicator for delivery of energy to target tissue. The energy applicator is provided with a surface-contact detection device. The energy applicator is operably associated with an electrosurgical power generating source. The method also includes the steps of transmitting energy from an electrosurgical power generating source through the energy applicator to the target tissue, monitoring whether a radiating portion of the energy applicator is disposed in contact with the target tissue based on a determination of whether optical signals generated by one or more optical transmitters of the surface-contact detection device associated with the energy applicator result in reflected optical signals received at one or more optical receivers of the surface-contact detection device and, if it is determined that optical signals generated by the one or more optical transmitters do not result in reflected optical signals received at the one or more optical receivers, cause cessation of energy delivery from the electrosurgical power generating source through the radiating portion to the target tissue.

In any one of the aspects, the one or more optical receivers may be photodiodes. In any one of the aspects, the one or more optical transmitters may be light-emitting diodes (LEDs).

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation-assisted resection. As it is used in this description, "energy applicator" generally refers to any device that can be used to transfer energy from a power generating source, such as a microwave or RF electrosurgical generator, to tissue.

As it is used in this description, "transmission line" generally refers to any transmission medium that can be used for the propagation of signals from one point to another. A transmission line may be, for example, a wire, a two-wire line, a coaxial wire, and/or a waveguide. Transmission lines such as microstrip, coplanar waveguide, stripline or coaxial may also be considered to be waveguides. As it is used in this description, "waveguide" generally refers to any linear structure that conveys electromagnetic waves between its endpoints.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or submultiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

As it is used in this description, "switch" or "switches" generally refers to any electrical actuators, mechanical actuators, electro-mechanical actuators (rotatable actuators, pivotable actuators, toggle-like actuators, buttons, etc.), optical actuators, or any suitable device that generally fulfills the purpose of connecting and disconnecting electronic devices, or component thereof, instruments, equipment, transmission line or connections and appurtenances thereto, or software.

Light may be regarded as an electromagnetic wave that travels in straight lines (gravity and electromagnetic influences excepted) until it is either reflected or refracted. Reflection of light occurs when the light waves encounter a surface or other boundary that does not absorb the energy of the radiation and bounces the waves away from the surface. Commonly, the incoming light wave is referred to as an incident (original) wave, and the wave that is bounced away from the surface is termed the reflected wave. As it is used in this description, "reflection coefficient" generally refers to a ratio of a reflected wave to an incident wave at a point of reflection. Refraction of light occurs when a light wave travels from a medium with a given refractive index to a medium with another refractive index. As it is used in this description, "refraction" generally refers to the change in direction of a wave due to a change in its speed, as occurs when a wave passes from one medium to another. As it is used in this description, "refractive index" generally refers to a measure of how much the speed of light is reduced inside a medium, compared to the speed of light in vacuum or air.

As it is used in this description, "light source" generally refers to all illumination sources including photo-luminescent sources, fluorescent sources, phosphorescence sources, lasers, electro-luminescent sources, such as electro-luminescent lamps, and light-emitting diodes. As it is used in this description, "light-emitting diode" generally refers to any system that is capable of receiving an electrical signal and producing a color of light in response to the signal. Thus, "light-emitting diode", as used herein, includes light-emitting diodes (LEDs) of all types, including white LEDs, infrared LEDs, ultraviolet LEDs, visible color LEDs, light-emitting polymers, semiconductor dies that produce light in response to current, organic LEDs, electro-luminescent strips, silicon based structures that emit light, and other such systems. As it is used in this description, "color" generally refers to any frequency of electromagnetic radiation, or combination of different frequencies, within the visible light spectrum, the infrared and ultraviolet areas of the spectrum, and in other areas of the electromagnetic spectrum where illumination sources may generate radiation.

As it is used in this description, "optical receiver" generally refers to a device that converts an incoming optical signal to an electrical signal. An optical receiver may include a transducer in the form of a detector, which may be a photodiode or other device. As it is used in this description, "optical transmitter" generally refers to a device that outputs an optical signal, including devices that convert an electrical signal into an optical signal.

BRIEF DESCRIPTION OF THE DRAWINGS

Objects and features of the presently-disclosed systems, devices and methods for optical detection of surface contact of an electrosurgical device to tissue and the presently-disclosed electrosurgical devices including a waveguide with removable dielectric structures will become apparent to those of ordinary skill in the art when descriptions of various embodiments thereof are read with reference to the accompanying drawings, of which:

FIG. 16 is a schematic diagram of yet another embodiment of an energy applicator that includes an antenna assembly including a waveguide with removable dielectric structures, shown with the surface-contact detection device of FIG. 8, with parts separated, in accordance with an of the present disclosure;

FIG. 17 is a schematic diagram of still another embodiment of an energy applicator that includes an antenna assembly including a waveguide with removable dielectric structures, shown with the surface-contact detection device of FIG. 8, with parts separated, in accordance with an of the present disclosure;

DETAILED DESCRIPTION

Figure 1:
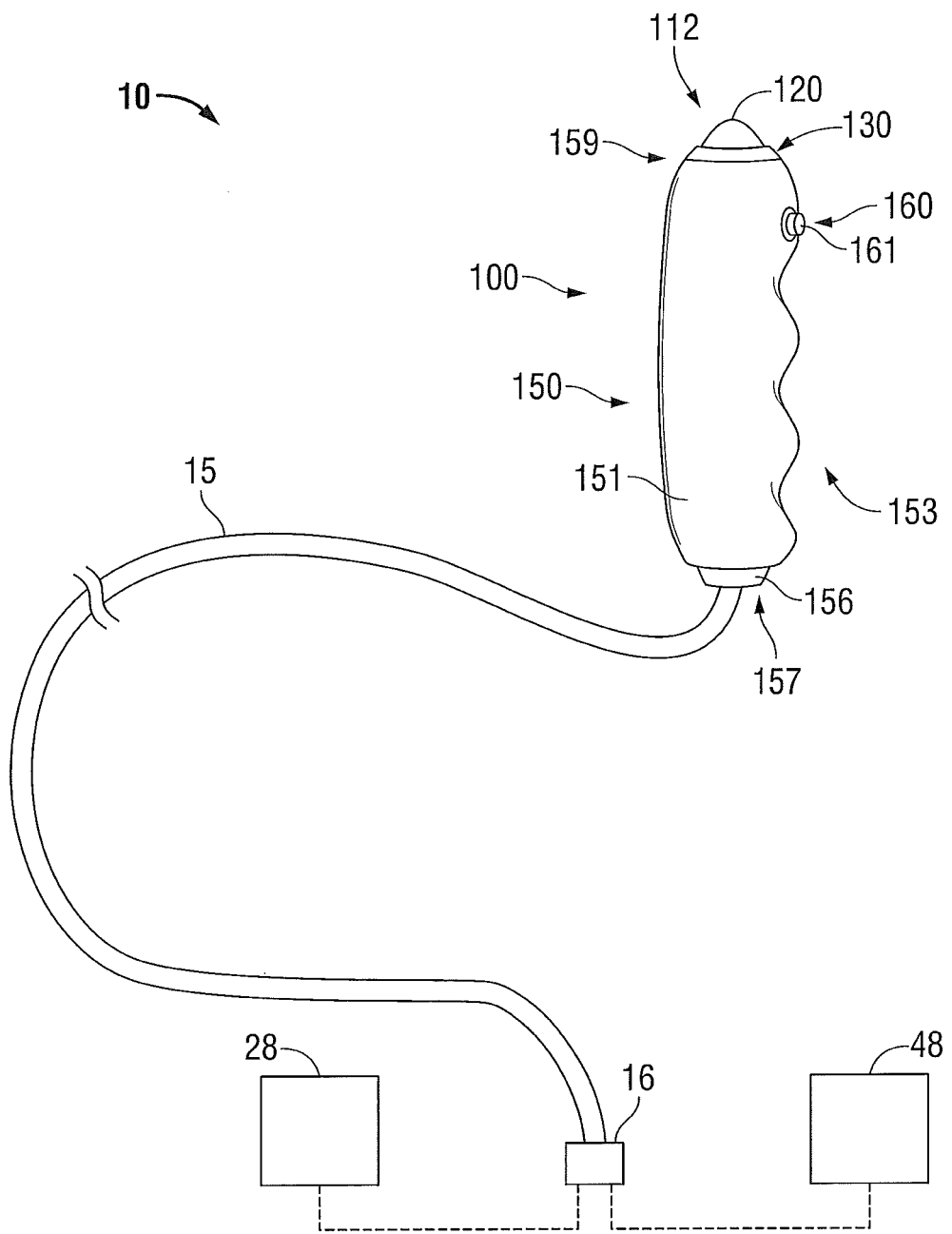
FIG. 1 is a schematic diagram of an electrosurgical system including an energy applicator provided with a surface-contact detection device in accordance with an embodiment of the present disclosure.

Hereinafter, embodiments of the presently-disclosed systems, devices and methods for optical detection of surface contact of an electrosurgical device to tissue and embodiments of the presently-disclosed electrosurgical devices including a waveguide with removable dielectric structures are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide electrosurgical devices for treating tissue. Various embodiments of the present disclosure provide systems, devices and methods for optical detection of surface-to-surface contact between an electrosurgical device surface and tissue. Embodiments may be implemented using electromagnetic radiation at microwave frequencies or at other frequencies. An electrosurgical system including an energy applicator including a surface-contact detection device, according to various embodiments, is configured to operate between about 300 MHz and about 10 GHz.

Various embodiments of the presently-disclosed electrosurgical systems including an energy applicator provided with a surface-contact detection device are suitable for microwave ablation and for use to pre-coagulate tissue for microwave ablation assisted surgical resection.

FIG. 1 shows an electrosurgical system (shown generally as 10) including an energy applicator 100. Energy applicator 100 includes an antenna assembly (shown generally as 280 in FIGS. 2 and 3), which is described in more detail later in this description, and a handle member 150 including a housing 151. A transmission line 15 may be provided to electrically couple the energy applicator 100 to an electrosurgical power generating source 28, e.g., a microwave or radio frequency (RF) electrosurgical generator. In some embodiments, as shown in FIG. 1, the energy applicator 100 is coupled via the transmission line 15 to a connector 16, which further operably connects the energy applicator 100 to the electrosurgical power generating source 28. Power generating source 28 may be any generator suitable for use with electrosurgical devices and may be configured to provide various frequencies of energy.

Figure 6:
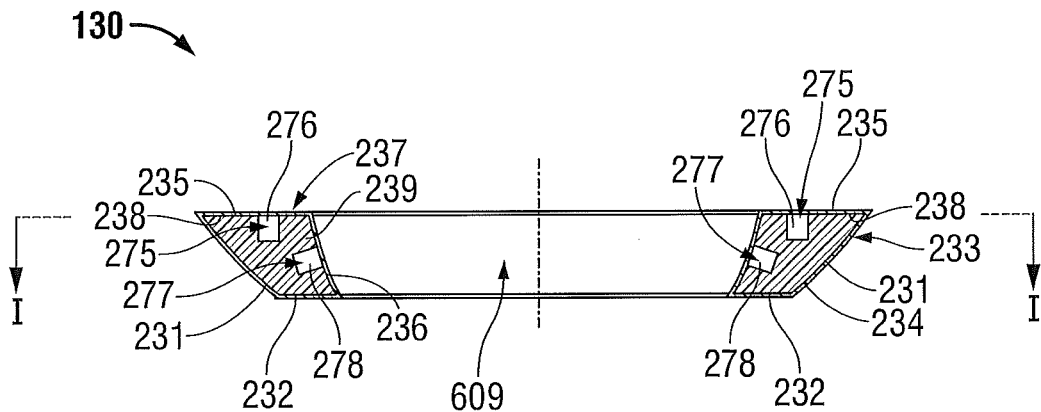
FIG. 6 is an enlarged, cross-sectional view of the surface-contact detection device shown in FIG. 1 in accordance with an embodiment of the present disclosure.
Figure 7:
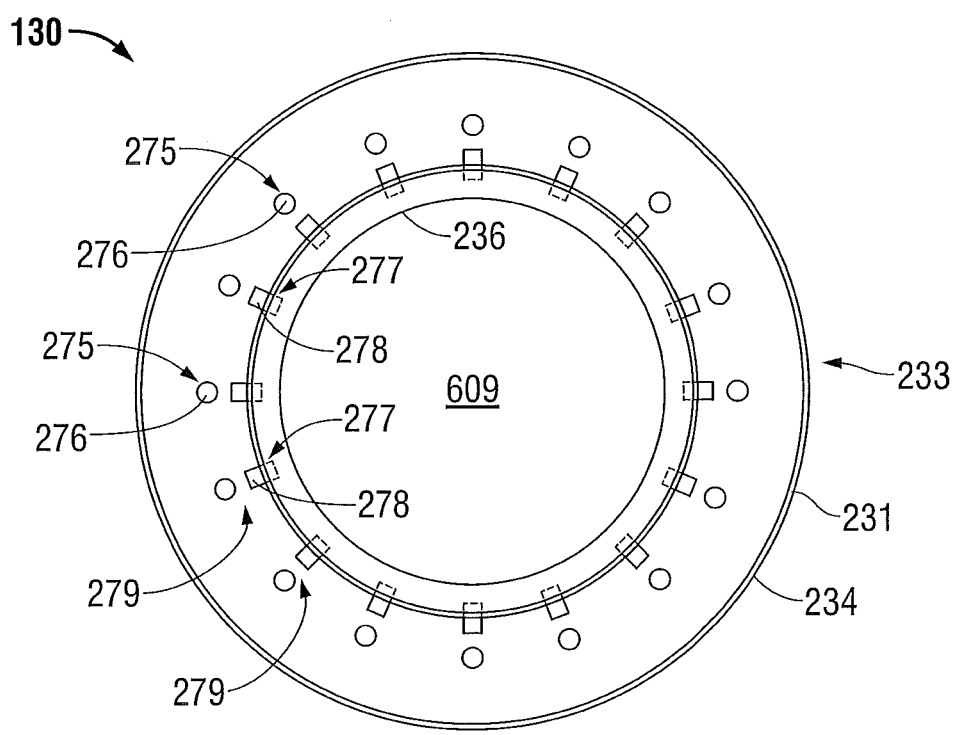
FIG. 7 is an enlarged, cross-sectional view taken along the section line I-I of FIG. 6.
Figure 8:
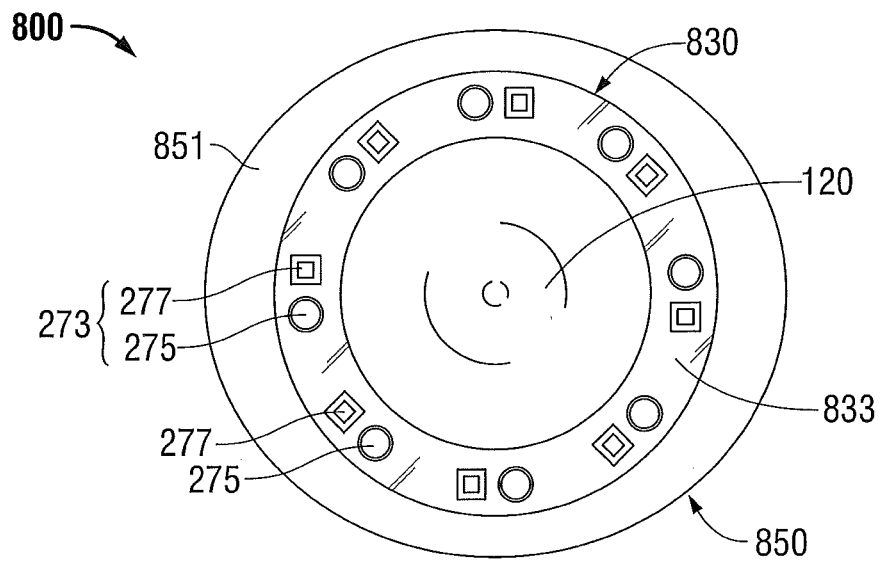
FIG. 8 is an enlarged, perspective view of a portion of an energy applicator and a surface-contact detection device coupled thereto in accordance with an embodiment of the present disclosure.
Figure 9:
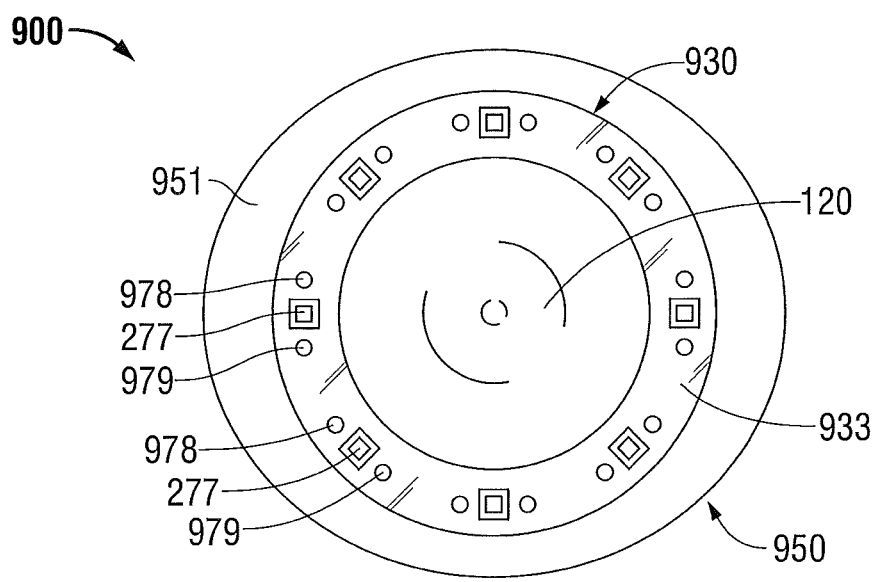
FIG. 9 is an enlarged, perspective view of a portion of an energy applicator and a surface-contact detection device coupled thereto in accordance with another embodiment of the present disclosure.

In some embodiments, the energy applicator 100 may be configured to be coupleable with a surface-contact detection device (e.g., surface-contact detection device 130 shown in FIGS. 2, 3, 6 and 7, surface-contact detection device 830 shown in FIG. 8, and surface-contact detection device 930 shown in FIG. 9). Surface-contact detection device 130 may include one or more connector portions (not shown) provided with one or more electrical connectors or terminals suitable for making electrical connections with certain of the circuitry of the handle member 150.

Figure 2:
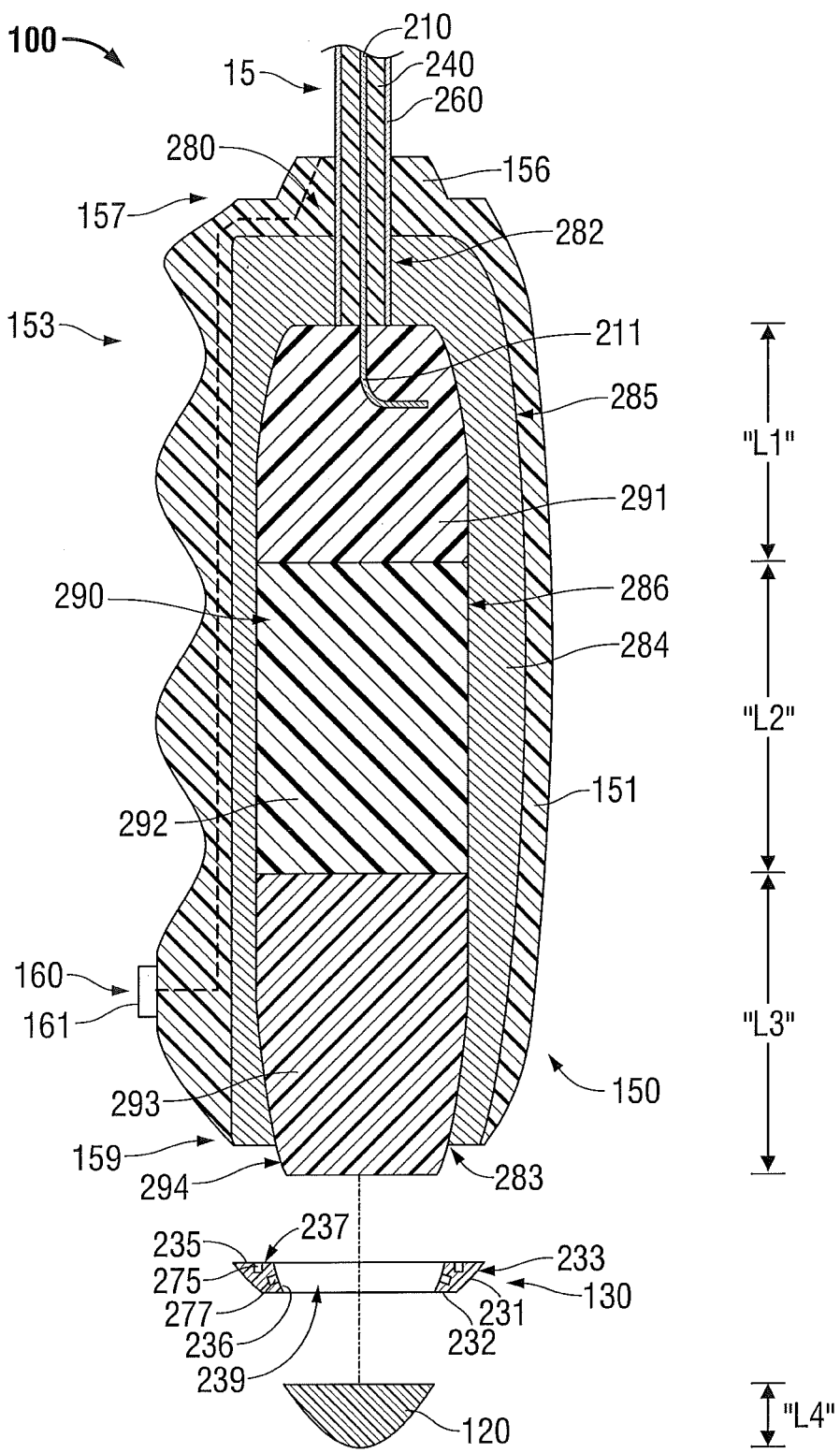
FIG. 2 is an enlarged, cross-sectional view of an embodiment of the energy applicator and the surface-contact detection device shown in FIG. 1, with parts separated, in accordance with the present disclosure.
Figure 3:
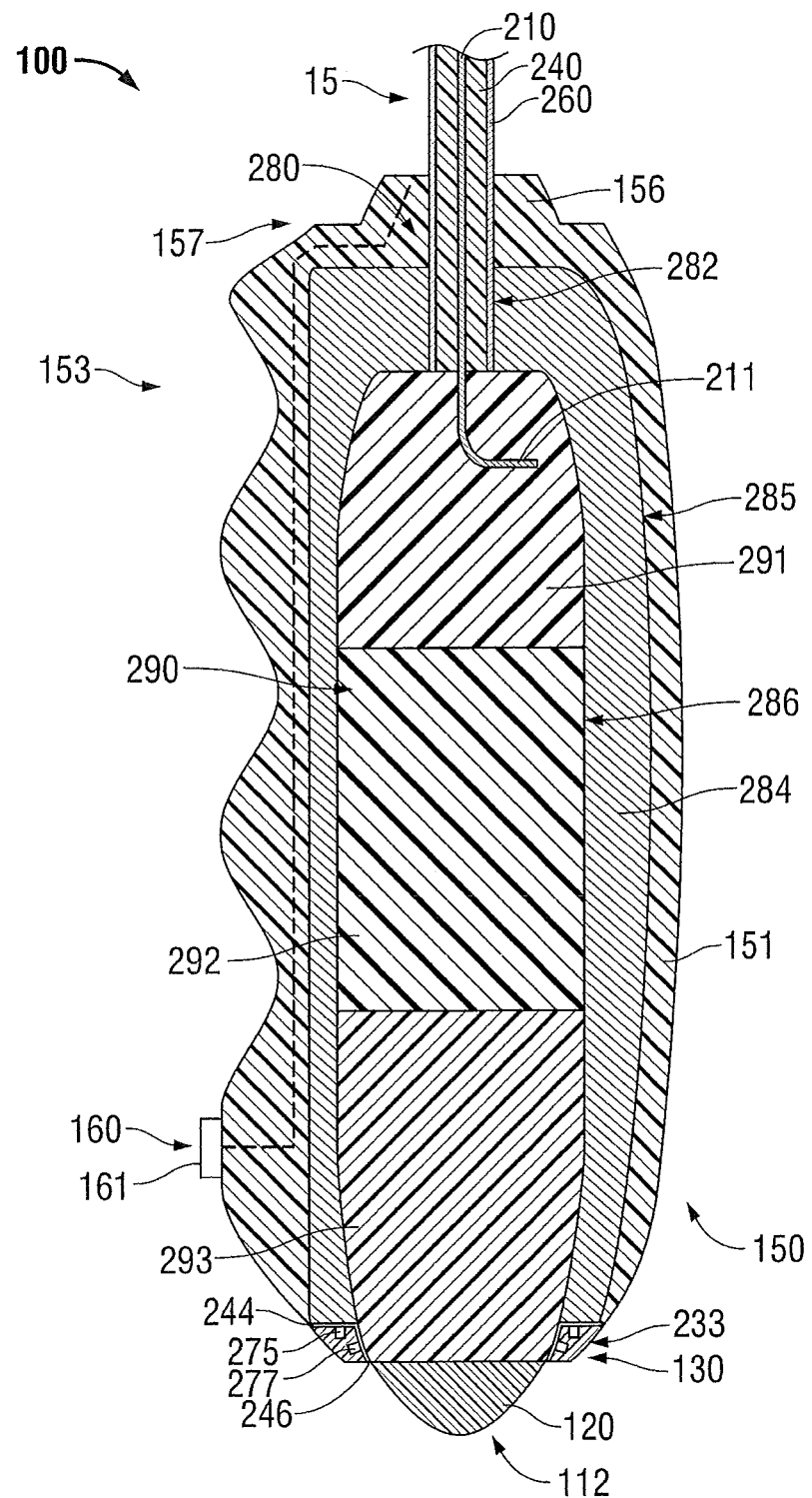
FIG. 3 is an enlarged, cross-sectional view of the assembled energy applicator of FIG. 2 shown in a configuration with the surface-contact detection device of FIG. 2 coupled to a distal end portion thereof in accordance with an embodiment of the present disclosure.

An embodiment of an energy applicator, such as the energy applicator 100 of the electrosurgical system 10 shown in FIG. 1, in accordance with the present disclosure, is shown in more detail in FIGS. 2 and 3. It will be understood, however, that other energy applicator embodiments (e.g., energy applicator 400 shown in FIGS. 4 and 5, and energy applicators 1400, 1500, 1600, 1700 and 1800 shown in FIGS. 14, 15, 16, 17 and 18, respectively) may also be used.

Housing 151 includes a grip portion 153 adapted to be gripped by the user, and may be formed of any suitable material, e.g., ceramic or polymeric materials. Grip portion 153 may have any suitable shape and may be provided with an ergonomic surface which is configured to be comfortably gripped by the hand of the user during operation of the instrument. In some embodiments, the energy applicator 100 may be adapted to be a reusable device. Autoclavable materials may be used to form the housing 151, and/or other components of the energy applicator 100, to provide for a sterilizable device.

Figure 4:
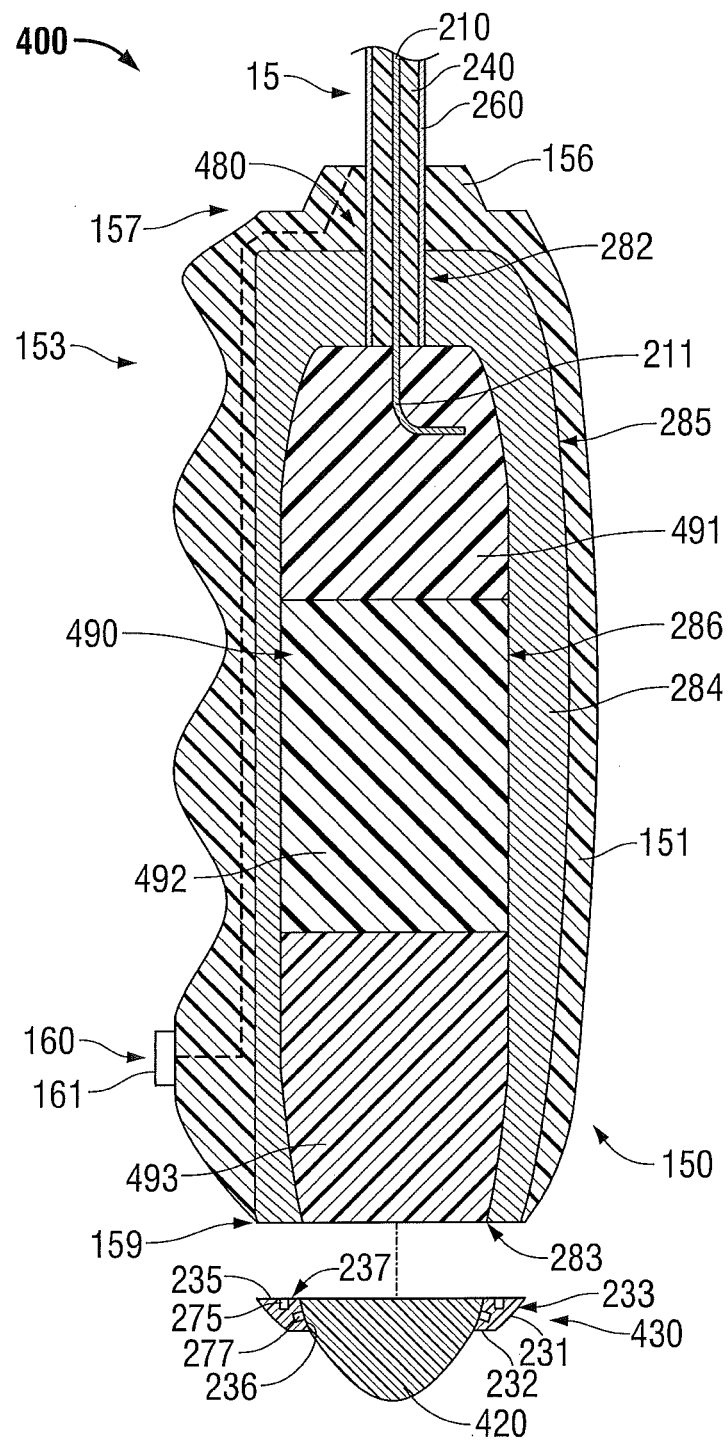
FIG. 4 is an enlarged, cross-sectional view of another embodiment of the energy applicator and the surface-contact detection device shown in FIG. 1, with parts separated, in accordance with the present disclosure.
Figure 5:
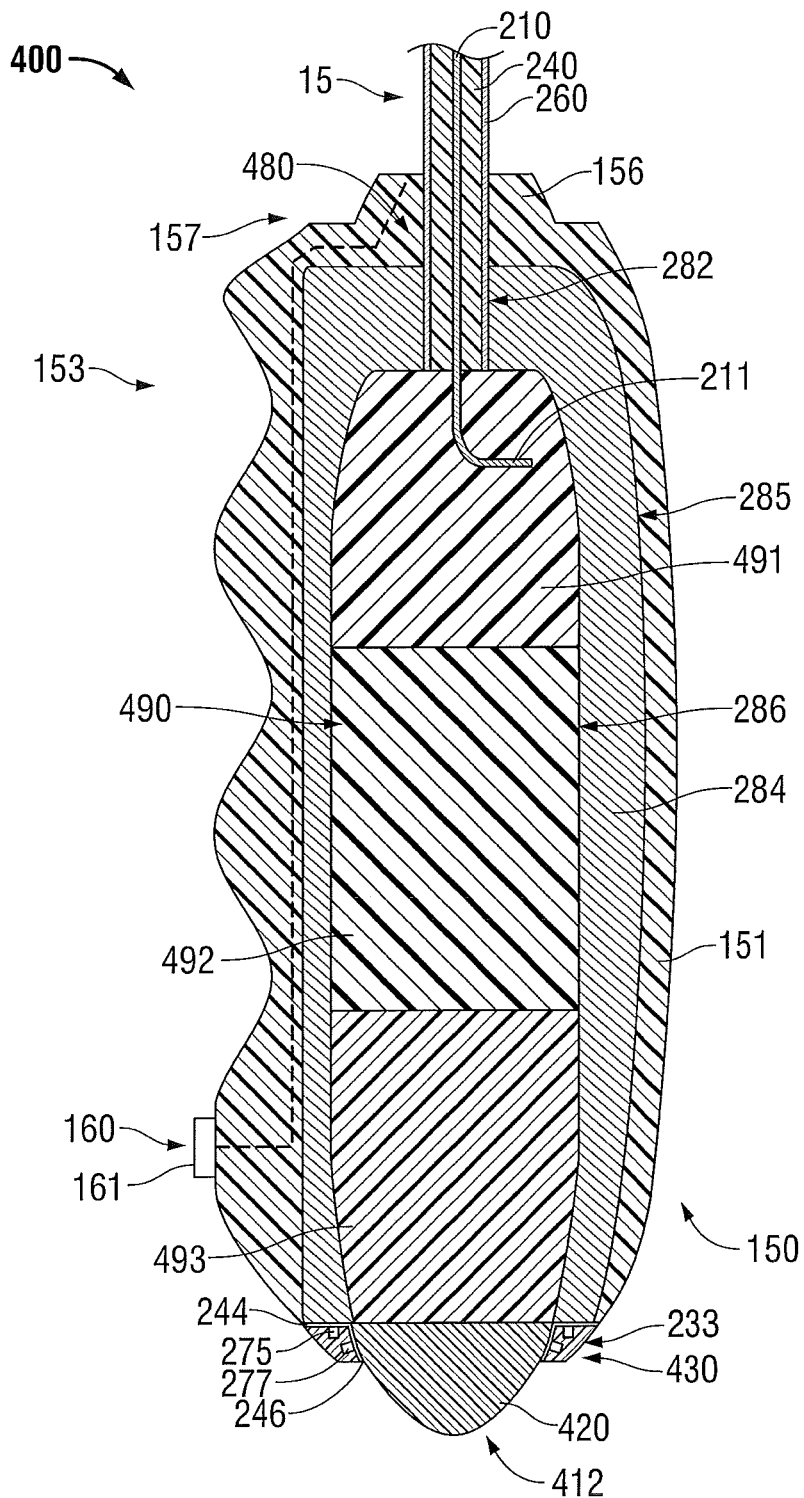
FIG. 5 is an enlarged, cross-sectional view of the assembled energy applicator of FIG. 4 shown in a configuration with the surface-contact detection device of FIG. 4 coupled to a distal end portion thereof in accordance with an embodiment of the present disclosure.

Energy applicator 100 may include a user interface 160 associated with the housing 151. In some embodiments, as shown in FIGS. 1, 2 and 4, the user interface 160 is disposed near the distal end 159 of the handle member 150. User interface 160 may include one or more controls 161 that may include without limitation a switch (e.g., pushbutton switch, toggle switch, slide switch) and/or a continuous actuator (e.g., rotary or linear potentiometer, rotary or linear encoder), and may have a desired ergonomic form. User interface 160 may be adapted to enable a user to selectively configure one or more operating parameters associated with the device, or component thereof, e.g., depending upon a particular purpose and/or to achieve a desired surgical outcome. User interface 160 may include an indicator unit (not shown) adapted to provide audio and/or other perceptible sensory alerts It is to be understood that the user interface 160 may be disposed at another location on the housing 151.

Based on one or more electrical signals generated by the user interface 160, a controller (not shown) and/or other circuitry (not shown) may adjust one or more operating parameters associated with the power generating source 28 and/or perform other control functions, alarming functions, or other functions in association therewith. The controller may be disposed within the power generating source 28, or located at the handle member 150 of the energy applicator 100. The controller may be a standalone unit. Some examples of operating parameters associated with the power generating source 28 that may be adjusted include temperature, impedance, power, current, voltage, mode of operation, and duration of application of electromagnetic energy.

In some embodiments, the housing 151 is formed from two housing halves (not shown). Each half of the housing 151 may include a series of mechanical interfacing components (not shown) configured to matingly engage with a corresponding series of mechanical interfaces (not shown) to align the two housing halves about the inner components and assemblies of the energy applicator 100. It is contemplated that the housing halves (as well as other components described herein) may be assembled together with the aid of alignment pins, snap-like interfaces, tongue and groove interfaces, locking tabs, adhesive ports, etc., utilized either alone or in combination for assembly purposes.

In some embodiments, as shown in FIGS. 1-5, the housing 151 includes a neck portion 156, e.g., disposed at the proximal end 157 of the handle member 150. Neck portion 156 defines an aperture therethrough configured to receive a portion of the transmission line 15 therein, and may be formed of any suitable material. Neck portion 156 may be formed of a rigid material and/or structurally reinforced with suitably rigid material, e.g., to enhance the reliability of the connection between the antenna assembly 280 and the transmission line 15. The shape and size of the neck portion 156 may be varied from the configuration depicted in FIGS. 1-5.

Housing 151 may be adapted to provide various configurations of electrical connections between the user interface 160, or component thereof (e.g., one or more controls 161), and one or more conductors for communicating control, feedback and/or identification signals between the energy applicator 100 and the power generating source 28. It is to be understood that the dotted lines indicative of electrical connections (e.g., electrical conductors) between various components of the energy applicator 100 shown in FIGS. 2-5 are merely illustrative and non-limiting examples of electrical connections, and that medical device embodiments of the present disclosure may utilize many different configurations of electrical connections, some with fewer, or additional, electrical connections than depicted in FIGS. 2-5. In some embodiments, a cable harness or the like may be disposed within the handle member 150, e.g., to allow communication between the detection device 130 and the user interface 160, or component thereof (e.g., one or more controls 161), and may be coupled via a cable bundle, e.g., disposed within the transmission line 15, to the power generating source 28.

Transmission line 15 includes an inner conductor 210 and an outer conductor 260, and may include a dielectric material 240 separating the inner conductor 210 and the outer conductor 260. In some embodiments, the inner conductor 210 is formed from a first electrically-conductive material (e.g., stainless steel) and the outer conductor 260 is formed from a second electrically-conductive material (e.g., copper). Inner conductor 210 and the outer conductor 260 may be formed from any suitable electrically-conductive material. Transmission line 15 may be cooled by fluid, e.g., saline or water, to improve power handling. Transmission line 15 may additionally, or alternatively, provide a conduit (not shown) configured to provide coolant from a coolant source 48 for cooling or buffering the energy applicator 100, e.g., deionized water, or other suitable cooling medium.

As shown in FIG. 3, the energy applicator 100 includes an antenna assembly 280 having a radiating portion 112. Referring to FIG. 2, the antenna assembly 280 includes a waveguide 285 with an open end 283 and a waveguide feed structure 282 having a coaxial line, e.g., distal portion of a coaxial line within the transmission line 15. Waveguide 285 includes electrically-conductive walls 284 of generally tubular shape, e.g., having a circular or rectangular cross section, and may be hollow or filled with a dielectric material. In some embodiments, the waveguide 285 may filled with a dielectric structure, e.g., a stack including two or more layers of dielectric material.

The waveguide walls 284 define a cavity 286 therein, and may include any electrically-conductive material, such as, for example, copper, stainless steel, titanium, titanium alloys such as nickel-titanium and titanium-aluminum-vanadium alloys, aluminum, aluminum alloys, tungsten carbide alloys, or combinations thereof. A portion 211 of the inner conductor 210 extends within the cavity 286. The cavity 286 is filled with a dielectric structure (shown generally as 290 in FIGS. 2 and 3). In some embodiments, the inner conductor 210 may terminate on the cavity wall. As seen in FIG. 2, the dielectric structure 290 includes a first dielectric layer 291 of length "L1", a second dielectric layer 292 of length "L2", and a third dielectric layer 293 of length "L3". The inner conductor 210 may terminate within any one of the first, second, or third dielectric layers 291, 292, or 293, respectively. The number, shape and length of the dielectric layers of the dielectric structure 290 (referred to hereinafter as the first dielectric structure 290) may be varied from the configuration depicted in FIGS. 2 and 3.

In some embodiments, as shown in FIGS. 2 and 3, a portion of the first dielectric structure 290 extends outwardly from the open end 283 of the waveguide 285. In other embodiments, the first dielectric structure (e.g., first dielectric structure 490 shown in FIGS. 4 and 5) is disposed entirely within the cavity 286 defined by the waveguide walls 284. The dielectric materials used to form the first dielectric structure 290 may vary in dielectric constant, e.g., to aid in radiation directivity and impedance matching and/or to achieve the optimum energy to tissue delivery. In some embodiments, the waveguide feed structure 282 may include a coaxial line to waveguide adapter (not shown), such as without limitation female and male type "N" or SMA connectors, or other electrical connector, which may be at least partially disposed within the neck portion 156 of the housing 151. In some embodiments, as shown in FIG. 2, a distal portion 294 of the third dielectric layer 293 extends outwardly from the open end 283 of the waveguide 285.

Energy applicator 100 may include a second dielectric structure disposed in proximity to the distal end 159 of the handle member 150, in association with the first dielectric structure 290. In some embodiments, as shown in FIGS. 2 and 3, the energy applicator 100 includes a second dielectric structure 120 of length "L4" configured to be coupleable with the distal end 294 (FIG. 2) of the third dielectric layer 293 of the first dielectric structure 290. Second dielectric structure 120 has a generally dome-like shape, but other configurations may be utilized, e.g., depending on the procedure to be performed, tissue characteristics of the target tissue or of the tissues adjacent thereto, etc. In some embodiments, the first dielectric structure 290 and the second dielectric structure 120 are configured to match the impedance of the transmission line 15 to the impedance of the target tissue.

Figure 10:
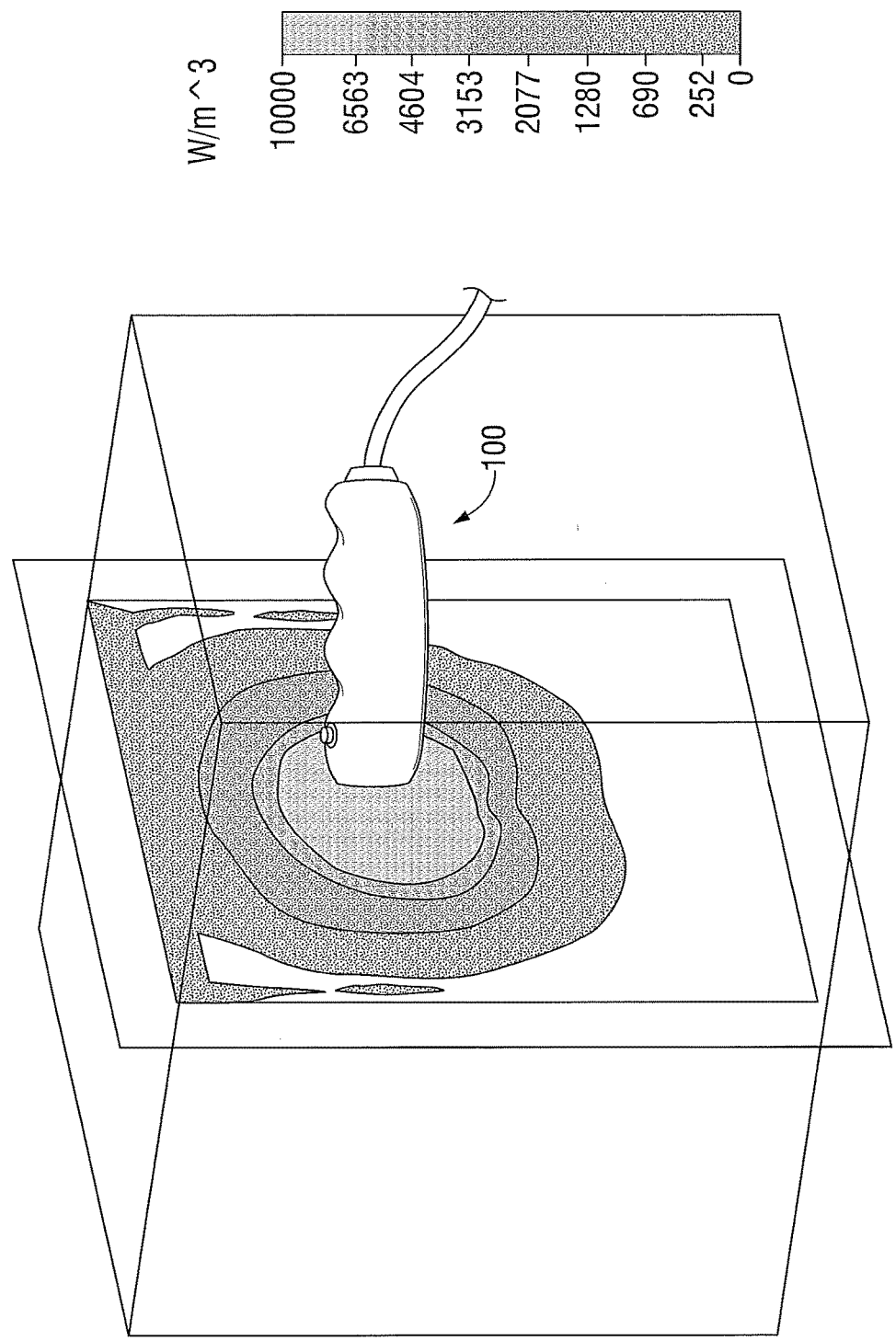
FIG. 10 is a diagrammatic representation of a radiation pattern of electromagnetic energy delivered into tissue by an energy applicator, such as the energy applicator of FIG. 1, in accordance with an embodiment of the present disclosure.

During microwave ablation, e.g., using the electrosurgical system 10, the energy applicator 100 is inserted into or placed adjacent to tissue and microwave energy is supplied thereto. FIG. 10 diagrammatically illustrates a radiation pattern of electromagnetic energy delivered into tissue by an energy applicator, such as the energy applicator 100 of FIG. 1. A clinician may pre-determine the length of time that microwave energy is to be applied. The duration of microwave energy application using the energy applicator 100 may depend on the progress of the heat distribution within the tissue area that is to be destroyed and/or the surrounding tissue. Electrosurgical system 10 may be adapted to cause cessation of energy delivery from the electrosurgical power generating source 28 through the radiating portion 112 of the energy applicator 100 to the target tissue based on an electrical signal transmitted by the surface-contact detection device 130, e.g., indicative of an alarm condition.

In operation, microwave energy having a wavelength, lambda (A), is transmitted through the antenna assembly 280, e.g., along the waveguide 285, the first dielectric structure 290 and/or the second dielectric structure 120, and radiated into the surrounding medium, e.g., tissue. The length of the antenna for efficient radiation may be dependent on the effective wavelength, $\lambda_{eff}$, which is dependent upon the dielectric properties of the medium being radiated into. Antenna assembly 280 through which microwave energy is transmitted at a wavelength, A, may have differing effective wavelengths, $\lambda_{eff}$, depending upon the surrounding medium, e.g., liver tissue, as opposed to breast tissue.

In some embodiments, the second dielectric structure 120 of FIGS. 2, 3 and 14-17 (and/or the second dielectric structure 420 shown in FIGS. 4 and 5) may be configured to be selectively detachable and/or removeably replaced, e.g., to allow selective matching of the impedance of the transmission line 15 to the impedance of a particular type or tissue. One or more dielectric layers of the first dielectric structure (e.g., the third dielectric layer 1493 of the first dielectric structure 1490 shown in FIG. 14, the second and/or third dielectric layers 1592 and/or 1593 of the first dielectric structure 1590 shown in FIG. 15, the third dielectric layer 1693 of the first dielectric structure 1690 shown in FIG. 16, and the second and third dielectric layers 1792 and 1793 of the first dielectric structure 1790 shown in FIG. 17) may additionally, or alternatively, be multi-configuration modular structures, and may be configured to be selectively removeably positioned/replaced, e.g., to allow selective matching of the impedance of the transmission line 15 to the impedance of a particular type or tissue.

A surface-contact detection device in accordance with embodiments of the present disclosure (e.g., surface-contact detection device 130 shown in FIGS. 2, 3, 6 and 7, surface-contact detection device 830 shown in FIG. 8, and surface-contact detection device 930 shown in FIG. 9) may be adapted for use with the energy applicator 100, and may be coupled, secured, or releaseably secured to the distal end 159 of the handle member 150 and/or the distal end of the waveguide walls 284.

Surface-contact detection device 130 has a generally ring-like configuration defined by a body member 237 and a lens member 233 and including a central opening 609 (FIGS. 6 and 7), e.g., configured to receive at least a portion of the distal portion 294 of the third dielectric layer 293 therein. In some embodiments, as shown in FIGS. 2 and 4, the body member 237 includes a first body element 235 and a second body element 236, which are coupled together and define an internal cavity 239. First body element 235 may be configured to engage the distal end 159 of the handle member 150 and/or the distal end of the waveguide walls 284. As seen in FIG. 6, the first body element 235 includes an inner surface 238, and the second body element 236 generally defines the central opening 609.

Body member 237, or portions thereof, may be coupled, secured, or releaseably secured to the distal end 159 of the handle member 150 (and/or the distal portion 294 of the third dielectric layer 293) using any suitable fastener mechanism, such as adhesive, mechanical interfacing components, etc. In some embodiments, the first body element 235 and the distal end 159 of the handle member 150 are bonded or otherwise joined together using an adhesive material 244, and/or the second body element 236 and the lateral surface of the distal portion 294 of the third dielectric layer 293 are bonded or otherwise joined together using an adhesive material 246. In alternative embodiments not shown, the surface-contact detection device 130 may be adapted to be removeably coupleable (e.g., threadedly coupleable) to the distal portion 294 of the third dielectric layer 293 that extends outwardly from the open end 283 of the waveguide 285 and/or removeably coupleable to the dielectric structure 120 or portion thereof.

Surface-contact detection device 130 generally includes one or more light source or light-emitting elements 275 (also referred to herein as optical transmitters 275) and one or more light-receiving elements 277 (also referred to herein as optical receivers 277). In various embodiments, one or more optical transmitters 275 may be coupled to the first body element 235 (and/or the second body element 236), and one or more optical receivers 277 may be coupled to the second body element 236 (and/or the first body element 235). Optical transmitters 275 may be any light source or suitable device configured to transmit optical signals, e.g., a light-emitting diode (LED) 276. LED 276 may be configured to transmit either a continuous or pulsed optical signal. Optical receivers 277 may include any suitable device configured to receive optical signals, e.g., a photo-diode 278. In various embodiments, at least one optical transmitter 275 and at least one optical receiver 277 are configured to communicate when the lens member 233 is disposed in intimate contact with tissue.

Energy applicator 100 may include one or more electrical conductors associated with the handle member 150 (and/or housing 151) for providing one or more electrically-conductive pathways. Surface-contact detection device 130 may include one or more connector portions provided with one or more electrical connectors or terminals suitable for making electrical connections with electrical conductors associated with the handle member 150 (and/or housing 151). The one or more connector portions may be configured to be removeably coupleable to electrical conductors associated with the handle member 150 (and/or housing 151).

Lens member 233 may be configured as a single pane (also referred to herein as a "lens element") or a plurality of panes, and may be formed of any suitable transparent or translucent material. In some embodiments, the lens member 233 may be formed of transparent or translucent material that by its material characteristics is reflective to optical signals transmitted by the optical transmitter 275 (e.g., emitted LED wavelength) when the lens member 233 is disposed in intimate contact with tissue, and transparent to the optical signals when there is no contact between the lens member 233 and tissue. In other embodiments, material suitable for forming the lens member 233 has material characteristics whereby the lens member 233 is transparent to optical signals transmitted by the optical transmitter 275 (e.g., emitted LED wavelength) when the lens member 233 is disposed in intimate contact with tissue, and reflective to the optical signals in the absence of contact between the lens member 233 and tissue.

Lens member 233 may include one or more lens elements of various shapes including flat and/or curved surfaces. Lens member 233 may include one or more lens elements, e.g., first lens element 231 and second lens element 232, having the same or different opacity. First lens element 231 and the second lens element 232 may be integrally formed as part of a unitary structure, if desired, or formed separately and joined together by any suitable process.

As best seen in FIG. 7, the surface-contact detection device 130 includes a plurality of optical transmitters 275 (e.g., LEDs 276) and a plurality of optical transmitters 275 (e.g., photo-diodes 278), wherein each respective optical transmitter 275 is individually paired with a different one of the optical receivers 277. Although the surface-contact detection device 130 shown in FIG. 7 is configured to include sixteen optical transmitter-receiver pairs 279, any suitable configuration of optical transmitters 275 and optical receivers 277 may be used. In some embodiments, a plurality of optical transmitters (e.g., first optical transmitter 978 and second optical transmitter 979 shown in FIG. 9) may be associated each optical receiver 277.

Each optical transmitter-receiver pair 279 includes an optical transmitter 275 (e.g., LED 276) disposed in a positional relation to the first lens element 231 so that optical signals transmitted by the optical transmitter 275 impinge on the first lens element 231. In some embodiments, the optical signals transmitted by each respective optical transmitter 275 are either, reflected by the first lens element 231 and impinge on an optical receiver 277, or not reflected by the first lens element 231 and do not impinge on the optical receiver 277, depending on whether the outer surface 234 of the first lens element 231 is disposed in intimate contact with tissue. When the lens member 233 is disposed in intimate contact with tissue, the first lens element 231 reflects optical signals transmitted by the optical transmitters 275 towards the optical receivers 277.

Figure 13:
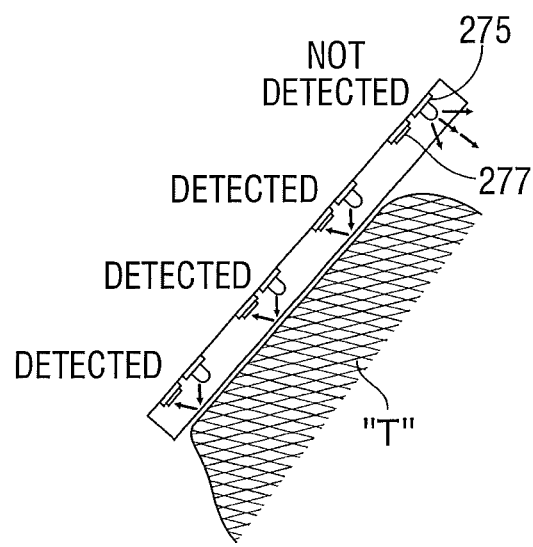
FIG. 13 is a schematic diagram of a portion of a surface-contact detection device shown with a first portion of the lens member disposed in contact with tissue, wherein the optical transmitters and the optical receivers associated with the first portion communicate, in accordance with an embodiment of the present disclosure.

In some embodiments, the absence of optical signals incident on each and every optical receiver 277 is interpreted as indicative that the distal radiating portion 112 of the energy applicator 100 is not disposed in contact with tissue. There may be circumstances wherein a first portion of a lens member (e.g., lens member 833 shown in FIG. 8) is disposed in contact with tissue "T" and a second portion is disposed in spaced relation to tissue "T", such as shown in FIG. 13, wherein the one or more optical transmitters 275 and optical receivers 277 associated with the first portion communicate, and the one or more optical transmitters 275 and optical receivers 277 associated with the second portion do not communicate. In some embodiments, the absence of optical signals incident on a predetermined number (or a number within a predetermined range) of the optical receivers 277 (e.g., all optical receivers 277 except for one or two) is interpreted as indicative that the distal radiating portion 112 of the energy applicator 100 is not disposed in contact with tissue.

In some embodiments, when the desired number of the optical receivers 277 have detected optical signals, the surface-contact detection device 130 transmits an electrical signal to an electrosurgical power generating source (e.g., electrosurgical power generating source 28 shown in FIG. 1) and, in response thereto, the power output of the power generating source may be reduced, e.g., for a predetermined time interval or until a manual reset switch is actuated.

In some embodiments, the presently-disclosed surface-contact detection devices may additionally include one or more sensors (not shown), such as without limitation, a temperature sensor, a power sensor to monitor forward and/or reflected power, and/or a radiation detector.

FIG. 8 shows a portion of an energy applicator (shown generally as 800) that includes a handle member 850 including a housing 851. Handle member 850 and the housing 851 are similar to the handle member 150 and the housing 151 shown in FIGS. 1-5 and further description thereof is omitted in the interests of brevity. In some embodiments, the energy applicator 800 includes a waveguide (e.g., waveguide 285 shown in FIGS. 2-5, or any one of the waveguides 1485, 1585, 1685 and 1785 shown in FIGS. 14, 15, 16 and 17, respectively), and may include a first dielectric structure (e.g., first dielectric structure 290 shown in FIGS. 2 and 3, first dielectric structure 490 shown in FIGS. 4 and 5, or any one of first dielectric structures 1490, 1590, 1690 and 1790 shown in FIGS. 14, 15, 16 and 17, respectively). Although the energy applicator 800 shown in FIG. 8 is provided with the second dielectric structure 120, other configurations may be utilized (e.g., second dielectric structure 420 shown in FIGS. 4 and 5).

Energy applicator 800 is provided with a surface-contact detection device 830 which may be coupled, secured, or releaseably secured to the distal end of the handle member 850 and/or the distal end of waveguide walls (e.g., waveguide walls 284 shown in FIGS. 2-5). Surface-contact detection device 830 may be provided with a configuration of one or more of electrical connectors for making electrical connections with one or more electrical connectors of the handle member 850 and/or other components of the energy applicator 800. Surface-contact detection device 830 includes a lens member 833, which may be formed of any suitable transparent or translucent material. Lens member 833 is similar to the lens member 233 shown in FIGS. 2-7 and further description thereof is omitted in the interests of brevity.

Surface-contact detection device 830 is similar to the surface-contact detection device 130 shown in FIGS. 1-7, except for the configuration of the optical transmitters 275 and the optical receivers 277. Surface-contact detection device 830 generally includes a plurality of optical transmitters 275 and a plurality of optical receivers 277, wherein each respective optical transmitter 275 is individually paired with a different one of the optical receivers 277. As seen in FIG. 8, the pairs 273 of optical transmitters 275 and the optical receivers 277 of the surface-contact detection device 830 are disposed in spaced apart relation to one another in a ring-like configuration, and may be disposed on a single surface (e.g., inner surface 238 of first body element 235 shown in FIG. 6).

FIG. 9 shows a portion of an energy applicator (shown generally as 900) that includes a handle member 950 including a housing 951. Handle member 950 and the housing 951 are similar to the handle member 150 and the housing 151 shown in FIGS. 1-5 and further description thereof is omitted in the interests of brevity. Energy applicator 900 may include a waveguide (e.g., waveguide 285 shown in FIGS. 2-5, or waveguides 1485, 1585, 1685 and 1785 shown in FIGS. 14, 15, 16 and 17, respectively), and may include a first dielectric structure (e.g., first dielectric structure 290 shown in FIGS. 2 and 3, first dielectric structure 490 shown in FIGS. 4 and 5, or first dielectric structure 1490, 1590, 1690 and 1790 shown in FIGS. 14, 15, 16 and 17, respectively) and/or the second dielectric structure 120.

Energy applicator 900 is provided with a surface-contact detection device 830. Surface-contact detection device 830 is adapted for use with the energy applicator 800, e.g., provided with a configuration of one or more electrical connectors for making electrical connections with one or more electrical connectors of the energy applicator 800, and may be coupled, secured, or releaseably secured to the distal end of the handle member 150 and/or the distal end of the waveguide walls (not shown). Surface-contact detection device 930 includes a lens member 933, which may be formed of any suitable transparent or translucent material. Lens member 933 is similar to the lens member 233 shown in FIGS. 2-7 and further description thereof is omitted in the interests of brevity.

Surface-contact detection device 930 is similar to the surface-contact detection device 830 shown in FIG. 8, except that the surface-contact detection device 930 includes two optical transmitters (also referred to herein as the first optical transmitter 978 and the second optical transmitters 979) disposed in association with each optical receiver 277, as opposed to the one-to-one correspondence of optical transmitters 275 and optical receivers 277 of the surface-contact detection device 830 shown in FIG. 8.

Figure 12:
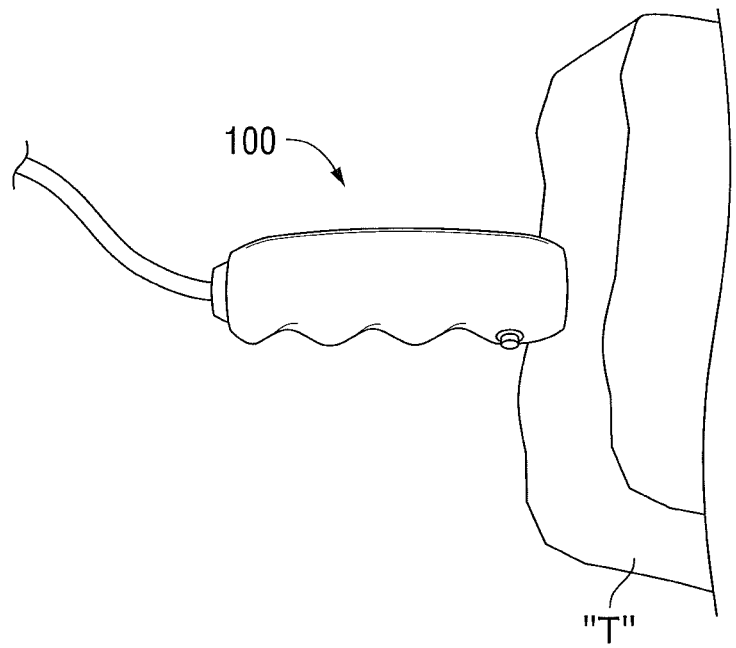
FIG. 12 is an enlarged, perspective view of an energy applicator, such as the energy applicator of FIG. 1, shown positioned for delivery of energy to tissue in accordance with an embodiment of the present disclosure.

FIG. 10 diagrammatically illustrates a radiation pattern of electromagnetic energy delivered into tissue "T" by an energy applicator, such as the energy applicator 100 shown in FIGS. 1 and 12, in accordance with an embodiment of the present disclosure.

Figure 11A:
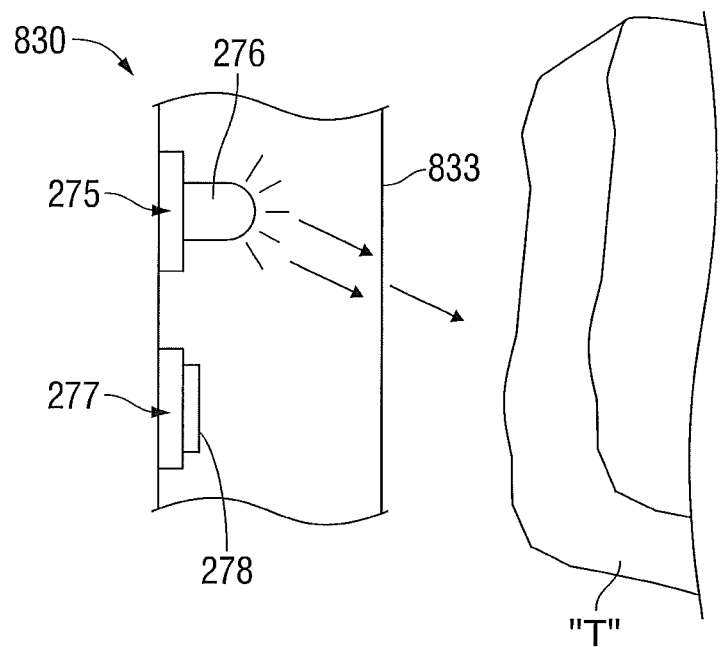
FIG. 11A is an enlarged, schematic view of a portion of a surface-contact detection device, such as the surface-contact detection device of FIG. 8, shown in a first configuration in which the lens member is disposed in spaced relation to tissue, wherein the optical transmitter and the optical receiver do not communicate, in accordance with an embodiment of the present disclosure.

FIG. 11A shows a portion of a surface-contact detection device (e.g., surface-contact detection device 830 shown in FIG. 8) disposed in a first configuration, wherein the lens member 833 is positioned in spaced relation to tissue "T". In this configuration, the optical signals transmitted by the optical transmitter 275 (e.g., LED 276) pass through the lens member 833. As a result, the optical transmitter 275 and the optical receiver 277 (e.g., photodiode 278) do not communicate.

Figure 11B:
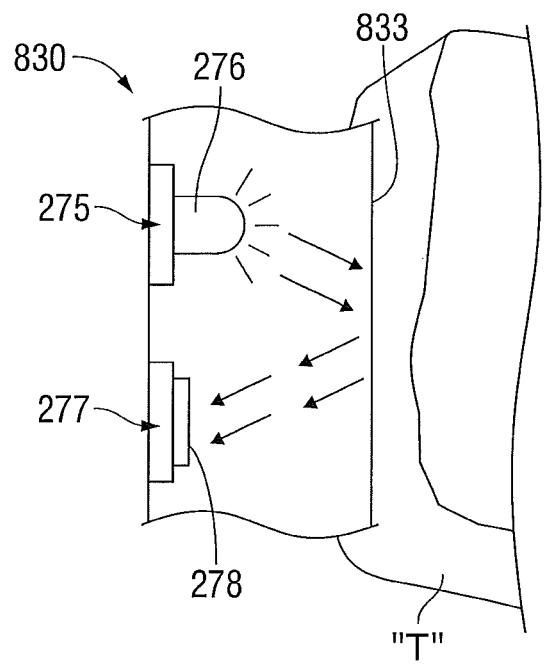
FIG. 11B is an enlarged, schematic view of a portion of a surface-contact detection device, such as the surface-contact detection device of FIG. 8, shown in a second configuration in which the lens member is disposed in contact with tissue, wherein the optical transmitter and the optical receiver communicate, in accordance with an embodiment of the present disclosure.

In FIG. 11B, the portion of the surface-contact detection device of FIG. 11A is shown disposed in a second configuration, wherein the lens member 833 is disposed in contact with tissue "T". In this configuration, the optical signals transmitted by the optical transmitter 275 (e.g., LED 276) are reflected by the lens member 833 and impinge upon the optical receiver 277 (e.g., photodiode 278). As a result, the optical transmitter 275 and the optical receiver 277 communicate.

FIG. 12 shows an energy applicator, such as the energy applicator 100 shown in FIG. 1, positioned for energy delivery into tissue "T". Electrosurgical systems in accordance with the present disclosure may be adapted to deliver energy from an electrosurgical power generating source 28 to the energy applicator 100 and/or to cause cessation of energy delivery from the electrosurgical power generating source 28 through the radiating portion 112 of the energy applicator 100 to tissue "T" based on one or more electrical signals transmitted by a surface-contact detection device (e.g., surface-contact detection device 130 shown in FIGS. 2, 3, 6 and 7, surface-contact detection device 830 shown in FIG. 8, or surface-contact detection device 930 shown in FIG. 9).

The various energy applicator embodiments shown in FIGS. 14-17 generally include an antenna assembly including a waveguide with removable dielectric structures, and may be configured to be coupleable with a surface-contact detection device (e.g., surface-contact detection device 130 shown in FIGS. 2, 3, 6 and 7, surface-contact detection device 830 shown in FIG. 8, or surface-contact detection device 930 shown in FIG. 9). The energy applicators 1400, 1500, 1600, 1700 and 1800 shown in FIGS. 14, 15, 16, 17 and 18, respectively, which are described in more detail below, may include any of the components of the energy applicator 100 shown in FIGS. 1-3.

Figure 14:
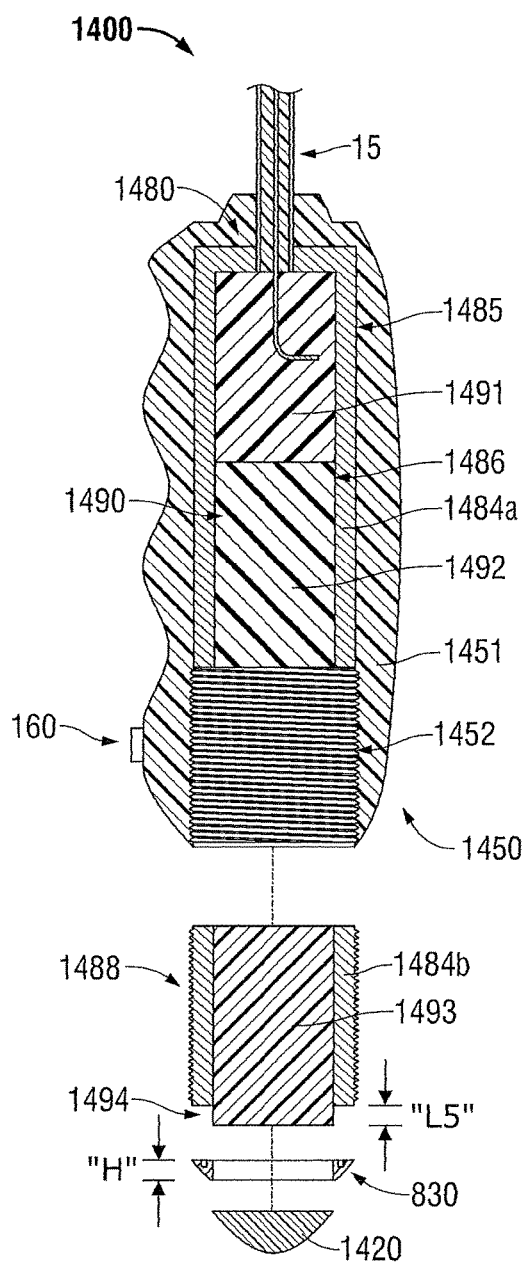
FIG. 14 is a schematic diagram of an energy applicator that includes an antenna assembly including a waveguide with removable dielectric structures, shown with the surface-contact detection device of FIG. 8, with parts separated, in accordance with an embodiment of the present disclosure.

FIG. 14 shows an energy applicator (shown generally as 1400) in accordance with an embodiment of the present disclosure that includes an antenna assembly 1480 including a waveguide 1485 with removable dielectric structures. Energy applicator 1400 includes a handle member 1450, and may include a user interface 160, e.g., disposed near the distal end of the handle member 1450. Handle member 1450 includes a housing 1451 including a threaded portion 1452. Handle member 1450 and the housing 1451 are similar to the handle member 150 and the housing 151, respectively, shown in FIGS. 1-3, except for the threaded portion 1452 of the housing 1451 shown in FIG. 14, and further description thereof is omitted in the interests of brevity.

Waveguide 1485 includes electrically-conductive walls 1484a, 1484b of generally tubular shape. The electrically-conductive walls 1484b including a threaded portion 1488 are separable from the housing 1451. The waveguide walls 1484a, 1484b define a cavity 1486 therein, and may be formed of any electrically-conductive material, such as without limitation, copper, stainless steel, titanium, titanium alloys such as nickel-titanium and titanium-aluminum-vanadium alloys, aluminum, aluminum alloys, tungsten carbide alloys, or combinations thereof.

The cavity 1486 is filled with a dielectric structure (shown generally as 1490, with parts separated, in FIG. 14) including a first dielectric layer 1491, a second dielectric layer 1492, and a third dielectric layer 1493. The dielectric materials used to form the first dielectric structure 1490 may vary in dielectric constant, e.g., to aid in radiation directivity and impedance matching and/or to achieve the optimum energy to tissue delivery. The shape, size and number of dielectric layers of the dielectric structure 1490 (referred to hereinafter as the first dielectric structure 1490) may be varied from the configuration depicted in FIG. 14.

As seen in FIG. 14, the third dielectric layer 1493 disposed in association with the electrically-conductive walls 1484b is configured to be separable from the housing 1451, e.g., to allow for the removal and replacement thereof. This provides the flexibility to modularly adapt and reconfigure the antenna assembly 1480, as desired, e.g., to match the impedance of the transmission line 15 to the impedance of tissue.

In some embodiments, the length of the threaded portion 1488 associated with the electrically-conductive walls 1484b is less than the length of the third dielectric layer 1493, e.g., to provide a space of adequate length "L5" to accommodate the surface-contact detection device 830 having height "H". Surface-contact detection device 830 may be coupled, secured, or releaseably secured to the distal end portion 1494 of the third dielectric layer 1493 and/or the distal end of the waveguide walls 1484b.

In some embodiments, as shown in FIG. 14, the energy applicator 1400 includes a second dielectric structure 1420 configured to be coupleable with the distal end portion 1494 of the first dielectric structure 1490. In other embodiments, a second dielectric structure (e.g., second dielectric structure 1820 shown in FIG. 18) may be configured to be coupleable with the distal end of the first dielectric structure and/or the distal end of the waveguide walls. Second dielectric structure 1420 has a generally dome-like shape, but other configurations may be utilized, e.g., depending on the procedure to be performed, tissue characteristics of the target tissue or of the tissues adjacent thereto, etc. Second dielectric structure 1420 is similar to the second dielectric structure 120 shown in FIGS. 1-3 and further description thereof is omitted in the interests of brevity.

Figure 15:
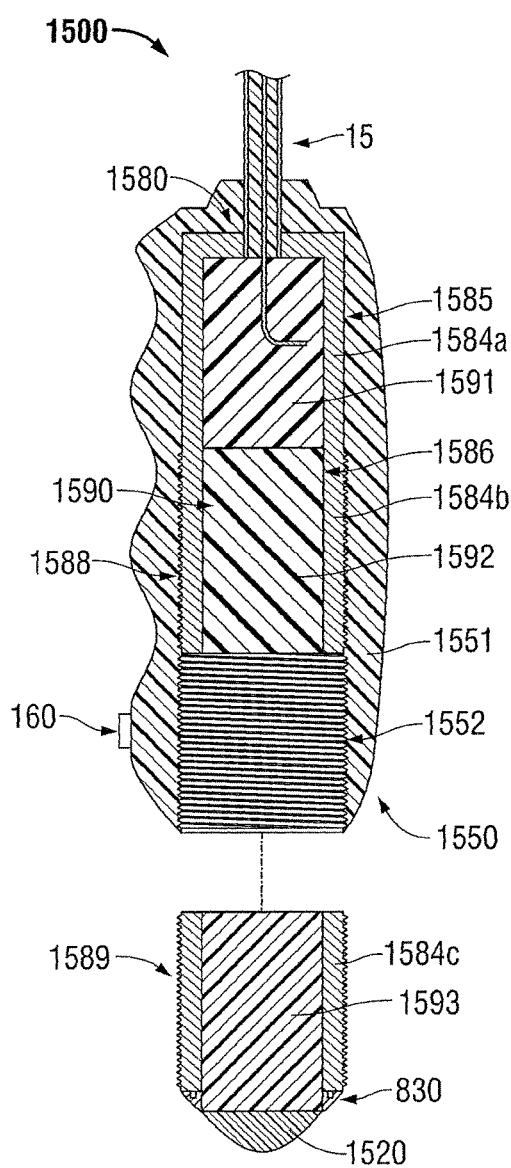
FIG. 15 is a schematic diagram of another embodiment of an energy applicator that includes an antenna assembly including a waveguide with removable dielectric structures, shown with the surface-contact detection device of FIG. 8, with parts separated, in accordance with an of the present disclosure.

FIG. 15 shows an energy applicator (shown generally as 1500) in accordance with an embodiment of the present disclosure that includes an antenna assembly 1580 including a waveguide 1585 with removable dielectric structures. Energy applicator 1500 includes a handle member 1550, and may include a user interface 160 disposed in association with the handle member 1550. Handle member 1550 includes a housing 1551 including a threaded portion 1552. Handle member 1550 and the housing 1551 are similar to the handle member 150 and the housing 151, respectively, shown in FIGS. 1-3, except for the threaded portion 1552 of the housing 1551 shown in FIG. 15, and further description thereof is omitted in the interests of brevity.

Waveguide 1585 includes electrically-conductive walls 1584a, 1584b and 1584c of generally tubular shape. The electrically-conductive walls 1584b including a first threaded portion 1588, and the electrically-conductive walls 1584c including a second threaded portion 1589 are individually separable from the housing 1551. The waveguide walls 1584a, 1584b and 1584c define a cavity 1586 therein, and may be formed of any suitable electrically-conductive material.

The cavity 1586 is filled with a dielectric structure (shown generally as 1590, with parts separated, in FIG. 15) including a first dielectric layer 1591, a second dielectric layer 1592, and a third dielectric layer 1593. The dielectric materials used to form the first dielectric structure 1590 may vary in dielectric constant, e.g., to aid in radiation directivity and impedance matching and/or to achieve the optimum energy to tissue delivery. The shape, size and number of dielectric layers of the dielectric structure 1590 (referred to hereinafter as the first dielectric structure 1590) may be varied from the configuration depicted in FIG. 15.

As seen in FIG. 15, the second and third dielectric layers 1592 and 1593 disposed in association with the electrically-conductive walls 1584b and 1584c, respectively, are configured to be separable from the housing 1551, e.g., to allow for the removal and replacement thereof. This provides the flexibility to modularly adapt and reconfigure the antenna assembly 1580, as desired, e.g., to match the impedance of the transmission line 15 to the impedance of tissue.

In some embodiments, as shown in FIG. 15, the energy applicator 1500 includes a second dielectric structure 1520 coupled to the distal end of the third dielectric layer 1593 of the first dielectric structure 1590. Second dielectric structure 1520 is similar to the second dielectric structure 120 shown in FIGS. 1-3 and further description thereof is omitted in the interests of brevity.

FIG. 16 shows an energy applicator (shown generally as 1600) in accordance with an embodiment of the present disclosure that includes an antenna assembly 1680 including a waveguide 1685 with removable dielectric structures. Energy applicator 1600 includes a handle member 1650 including a housing 1651, which are similar to the handle member 150 and the housing 151, respectively, shown in FIGS. 1-3 and further description thereof is omitted in the interests of brevity. Energy applicator 1600 may include a user interface 160 disposed in association with the handle member 1650.

Waveguide 1685 includes electrically-conductive walls 1684 of generally tubular shape, and may be formed of any suitable electrically-conductive material. The waveguide walls 1684 define a cavity 1686 therein and include a threaded portion 1652. The cavity 1686 is filled with a dielectric structure (shown generally as 1690, with parts separated, in FIG. 16) including a first dielectric layer 1691, a second dielectric layer 1692, and a third dielectric layer 1693. The third dielectric layer 1693 includes a threaded portion 1694. The dielectric materials used to form the first dielectric structure 1690 may vary in dielectric constant, e.g., to aid in radiation directivity and impedance matching and/or to achieve the optimum energy to tissue delivery. The shape, size and number of dielectric layers of the dielectric structure 1690 (referred to hereinafter as the first dielectric structure 1690) may be varied from the configuration depicted in FIG. 16.

As seen in FIG. 16, the third dielectric layer 1693 is configured to be separable from the waveguide 1685, e.g., to allow for the removal and replacement thereof. This provides the flexibility to modularly adapt and reconfigure the antenna assembly 1680, as desired, e.g., to match the impedance of the transmission line 15 to the impedance of tissue.

In some embodiments, as shown in FIG. 16, the energy applicator 1600 includes a second dielectric structure 1620 coupled to the distal end of the third dielectric layer 1693 of the first dielectric structure 1690. Second dielectric structure 1620 has a generally dome-like shape, but other configurations may be utilized. Second dielectric structure 1620 is similar to the second dielectric structure 120 shown in FIGS. 1-3 and further description thereof is omitted in the interests of brevity.

FIG. 17 shows an energy applicator (shown generally as 1700) in accordance with an embodiment of the present disclosure that includes an antenna assembly 1780 including a waveguide 1785 with removable dielectric structures. Energy applicator 1700 includes a handle member 1750 including a housing 1751, which are similar to the handle member 150 and the housing 151, respectively, shown in FIGS. 1-3 and further description thereof is omitted in the interests of brevity. Energy applicator 1700 may include a user interface 160 disposed in association with the handle member 1750.

Waveguide 1785 includes electrically-conductive walls 1784 of generally tubular shape, and may be formed of any suitable electrically-conductive material. The waveguide walls 1784 define a cavity 1786 therein and include a threaded portion 1752. The cavity 1786 is filled with a dielectric structure (shown generally as 1790, with parts separated, in FIG. 17) including a first dielectric layer 1791, a second dielectric layer 1792, and a third dielectric layer 1793. The second dielectric layer 1792 includes a threaded portion 1795. The third dielectric layer 1793 includes a threaded portion 1794. The dielectric materials used to form the first dielectric structure 1790 may vary in dielectric constant, e.g., to aid in radiation directivity and impedance matching and/or to achieve the optimum energy to tissue delivery. The shape, size and number of dielectric layers of the dielectric structure 1790 (referred to hereinafter as the first dielectric structure 1790) may be varied from the configuration depicted in FIG. 17.

As seen in FIG. 17, the second and third dielectric layers 1792 and 1793, respectively, are configured to be separable from the waveguide 1785, e.g., to allow for the removal and replacement thereof. This provides the flexibility to modularly adapt and reconfigure the antenna assembly 1780, as desired, e.g., to match the impedance of the transmission line 15 to the impedance of tissue.

In some embodiments, as shown in FIG. 17, the energy applicator 1700 includes a second dielectric structure 1720 coupled to the distal end of the third dielectric layer 1793 of the first dielectric structure 1790. Second dielectric structure 1720 has a generally dome-like shape, but other configurations may be utilized. Second dielectric structure 1720 is similar to the second dielectric structure 120 shown in FIGS. 1-3 and further description thereof is omitted in the interests of brevity.

Figure 18:
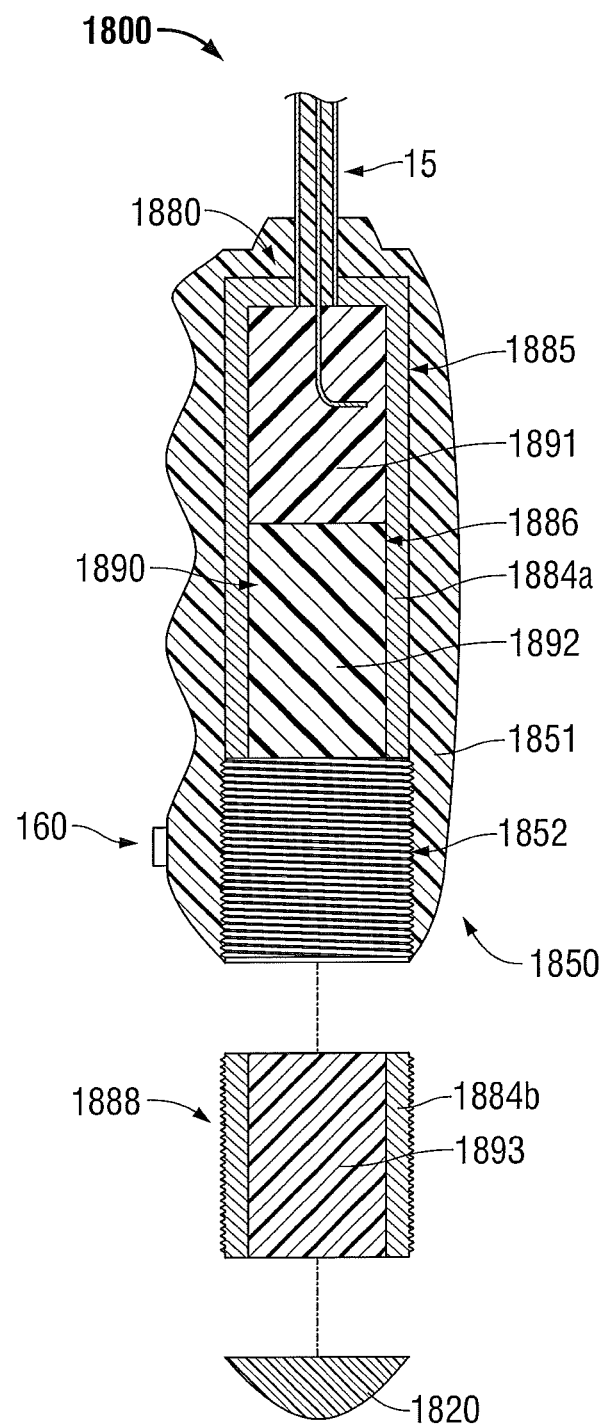
FIG. 18 is a schematic diagram of still another embodiment of an energy applicator that includes an antenna assembly including a waveguide with removable dielectric structures, with parts separated, in accordance with an of the present disclosure.

FIG. 18 shows an energy applicator (shown generally as 1800) in accordance with an embodiment of the present disclosure that includes an antenna assembly 1880 including a waveguide 1885 with removable dielectric structures. Energy applicator 1800 includes a handle member 1850, and may include a user interface 160 disposed in association therewith. Handle member 1850 includes a housing 1851 including a threaded portion 1852. Handle member 1850 and the housing 1851 are similar to the handle member 150 and the housing 151, respectively, shown in FIGS. 1-3, except for the threaded portion 1852 of the housing 1851 shown in FIG. 18, and further description thereof is omitted in the interests of brevity.

Waveguide 1885 includes electrically-conductive walls 1884*a* and 1884*b* of generally tubular shape including a threaded portion 1888. The electrically-conductive walls 1484*b* associated with the threaded portion 1888 are separable from the housing 1851. The waveguide walls 1884*a* and 1884*b* define a cavity 1886 therein, and may be formed of any electrically-conductive material, e.g., copper, stainless steel, titanium, titanium alloys such as nickel-titanium and titanium-aluminum-vanadium alloys, aluminum, aluminum alloys, tungsten carbide alloys, or combinations thereof.

The cavity 1886 is filled with a dielectric structure (shown generally as 1890, with parts separated, in FIG. 18) including a first dielectric layer 1891, a second dielectric layer 1892, and a third dielectric layer 1893. The dielectric materials used to form the first dielectric structure 1890 may vary in dielectric constant, e.g., to aid in radiation directivity and impedance matching and/or to achieve the optimum energy to tissue delivery. The shape, size and number of dielectric layers of the dielectric structure 1890 (referred to hereinafter as the first dielectric structure 1890) may be varied from the configuration depicted in FIG. 18.

As seen in FIG. 18, the third dielectric layer 1893 disposed in association with the electrically-conductive walls 1884*b* is configured to be separable from the housing 1851, e.g., to allow for the removal and replacement thereof. This provides the flexibility to modularly adapt and reconfigure the antenna assembly 1880, as desired, e.g., to match the impedance of the transmission line 15 to the impedance of tissue.

In some embodiments, as shown in FIG. 18, the energy applicator 1800 includes a second dielectric structure 1820 configured to be coupleable with the distal end of the first dielectric structure 1890 and/or the distal end of the waveguide walls 1884*b*. Second dielectric structure 1820 has a generally dome-like shape, but other configurations may be utilized, e.g., depending on the procedure to be performed, tissue characteristics of the target tissue or of the tissues adjacent thereto, etc.

Hereinafter, methods of directing energy to tissue, in accordance with the present disclosure, are described with reference to FIGS. 19 through 21. It is to be understood that the steps of the methods provided herein may be performed in combination and in a different order than presented herein without departing from the scope of the disclosure.

Figure 19:
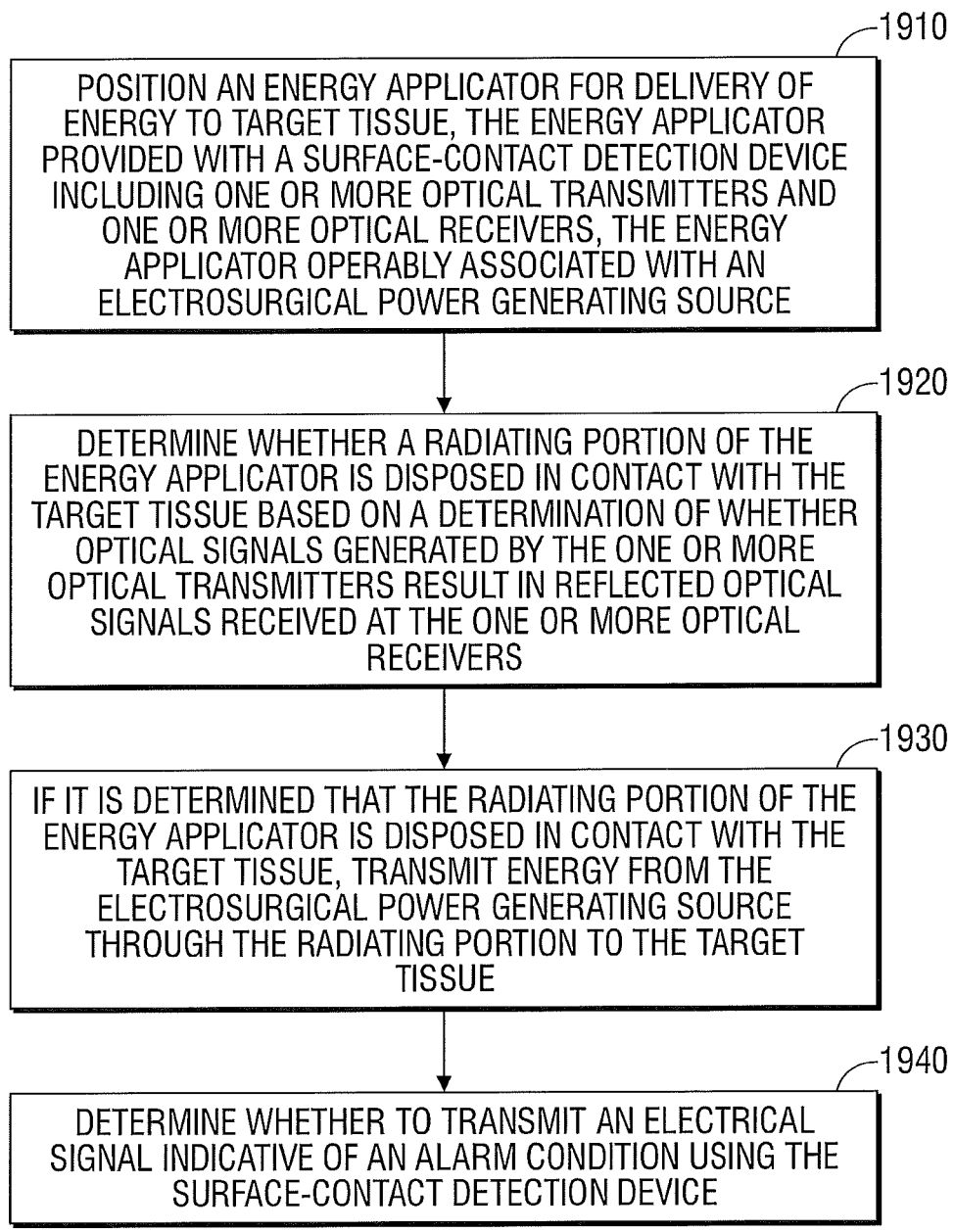
FIG. 19 is a flowchart illustrating a method of directing energy to tissue in accordance with an embodiment of the present disclosure.

FIG. 19 is a flowchart illustrating a method of directing energy to tissue according to an embodiment of the present disclosure. In step 1910, an energy applicator 100 is positioned for delivery of energy to target tissue "T". The energy applicator 100 is provided with a surface-contact detection device 130 that includes one or more optical transmitters 275 and one or more optical receivers 277. The energy applicator 100 is operably associated with an electrosurgical power generating source 28. In some embodiments, the optical transmitters 275 may be LEDs 276 and/or the optical receivers 277 may be photodiodes 278.

In step 1920, a determination is made whether a radiating portion 112 of the energy applicator 100 is disposed in contact with the target tissue "T" based on a determination of whether optical signals generated by the one or more optical transmitters 275 result in reflected optical signals received at the one or more optical receivers 277.

If it is determined, in step 1920, that the radiating portion of the energy applicator 100 is disposed in contact with target tissue "T", then, in step 1930, energy is transmitted from the electrosurgical power generating source 28 through the radiating portion 112 to the target tissue "T".

In an optional step 1940, a determination is made whether to transmit an electrical signal indicative of an alarm condition using the surface-contact detection device 130.

In some embodiments, an electrical signal indicative of an alarm condition is transmitted based on an absence of optical signals incident on each one of the one or more optical receivers 277. One or more operating parameters associated with the electrosurgical power generating source 28 may be adjusted in response to the electrical signal. Some examples of operating parameters associated with the power generating source 28 that may be adjusted include temperature, impedance, power, current, voltage, mode of operation, and duration of application of electromagnetic energy.

Figure 20:
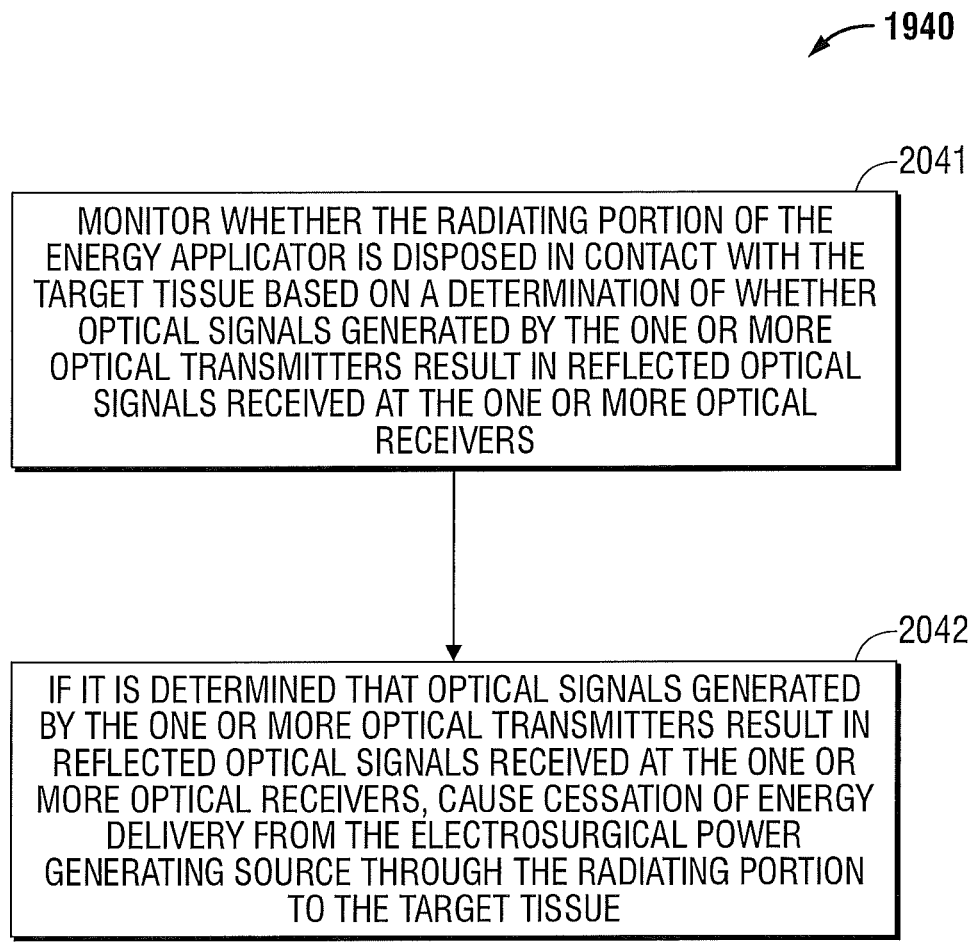
FIG. 20 is a flowchart illustrating an embodiment of the step of determining whether to transmit an electrical signal indicative of an alarm condition of the method illustrated in FIG. 19 in accordance with the present disclosure.

As illustrated in FIG. 20, step 1940 may further include steps 2041 and 2042. In step 2041, monitor whether the radiating portion 112 of the energy applicator 100 is disposed in contact with the target tissue "T" based on a determination of whether optical signals generated by the one or more optical transmitters 275 result in reflected optical signals received at the one or more optical receivers 277 of the surface-contact detection device.

In step 2041, if it is determined that optical signals generated by the one or more optical transmitters 275 do not result in reflected optical signals received at the one or more optical receivers 277, cause cessation of energy delivery from the electrosurgical power generating source 28 through the radiating portion 112 to the target tissue "T".

Figure 21:
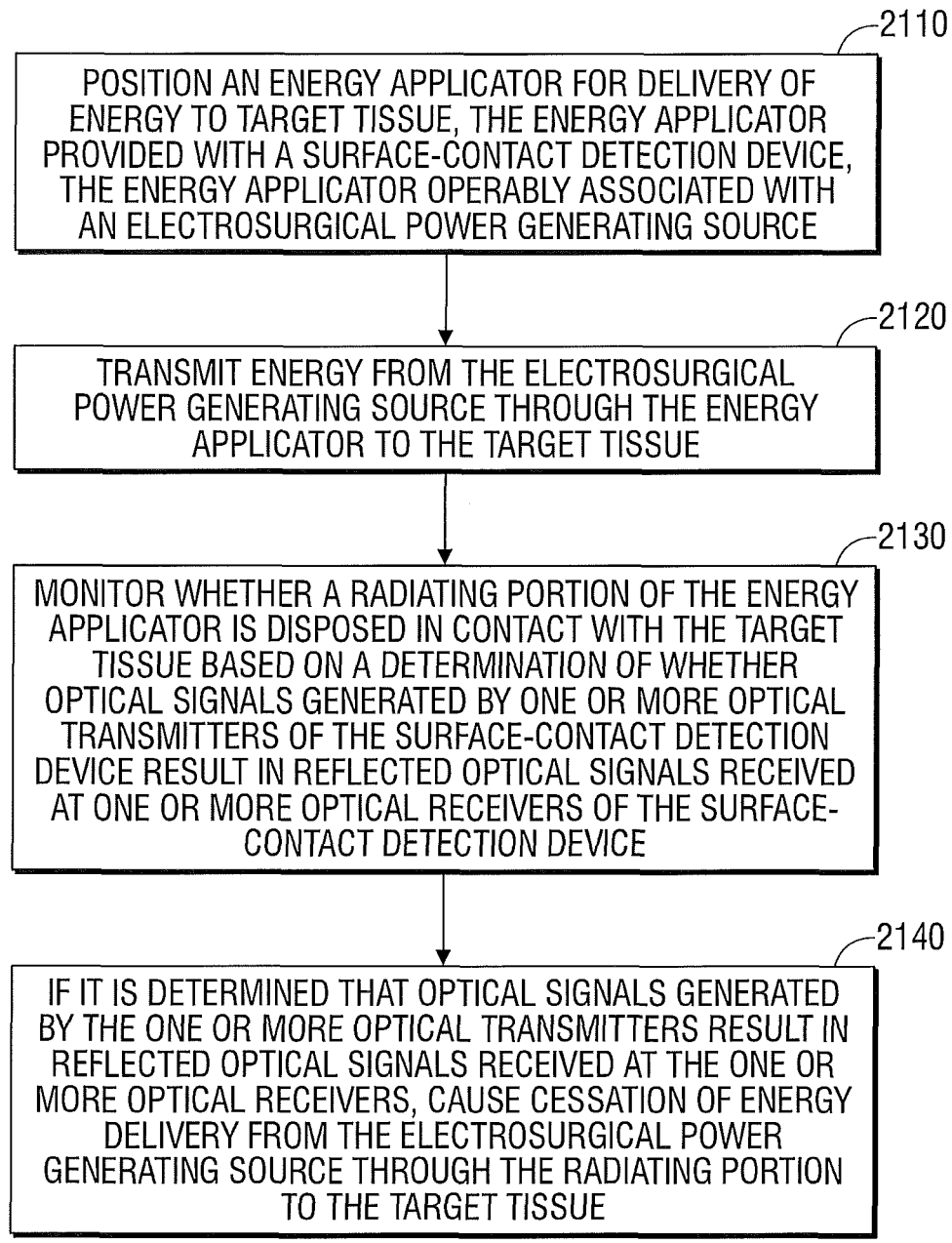
FIG. 21 is a flowchart illustrating a method of directing energy to tissue in accordance with another embodiment of the present disclosure.

FIG. 21 is a flowchart illustrating a method of directing energy to tissue according to an embodiment of the present disclosure. In step 2110, an energy applicator 100 is positioned for delivery of energy to target tissue "T". The energy applicator 100 is operably associated with an electrosurgical power generating source 28.

In step 2120, energy is transmitted from the electrosurgical power generating source 28 through the energy applicator to the target tissue "T".

In step 2130, monitor whether a radiating portion 112 of the energy applicator 100 is disposed in contact with the target tissue "T" based on a determination of whether optical signals generated by one or more optical transmitters 275 of the surface-contact detection device result in reflected optical signals received at one or more optical receivers 277 of the surface-contact detection device 130. In some embodiments, the optical transmitters 275 may be LEDs 276 and/or the optical receivers 277 may be photodiodes 278.

If it is determined, in step 2130, that the optical signals generated by the one or more optical transmitters 275 do not result in reflected optical signals received at the one or more optical receivers 277, then, in step 2140, cause cessation of energy delivery from the electrosurgical power generating source 28 through the radiating portion 112 to the target tissue "T".

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical device, comprising:
   a surface-contact detection device including:
      a first body element;
      a second body element coupled to the first body element, the second body element defining a central opening through the surface-contact detection device;
      a lens member coupled to the first and second body elements such that an internal cavity is defined between the lens member and the first and second body elements, the lens member disposed laterally offset from the central opening;
      at least one optical transmitter disposed within the internal cavity and coupled to the first body element, the at least one optical transmitter configured to generate optical signals; and
      at least one optical receiver disposed within the internal cavity and coupled to the second body element, the at least one optical receiver configured to receive optical signals reflected by the lens member,
      wherein the lens member is adapted to allow the at least one optical transmitter and the at least one optical receiver to communicate when the lens member is disposed in contact with tissue; and
   a dielectric structure disposed at least partially within the central opening defined through the surface-contact detection device.

2. The electrosurgical device of claim 1, wherein the lens member is configured to reflect optical signals generated by the at least one optical transmitter when the lens member is disposed in contact with tissue.

3. The electrosurgical device of claim 1, further comprising a handle member, the surface-contact detection device configured to couple to a distal end of the handle member.

4. The electrosurgical device of claim 3, further comprising a waveguide disposed at least partially within the handle member.

5. The electrosurgical device of claim 4, wherein the surface-contact detection device is coupled to a distal end of the waveguide.

6. The electrosurgical device of claim 3, further comprising a dielectric layer disposed within the handle member, the dielectric layer coaxially aligned with the central opening defined through the surface-contact detection device.

7. The electrosurgical device of claim 1, wherein the at least one optical transmitter includes a light-emitting diode.

8. The electrosurgical device of claim 1, wherein the at least one optical receiver includes a photodiode.

9. The electrosurgical device of claim 1, wherein the dielectric structure extends distally of a distal end of the central opening defined through the surface-contact detection device.

10. The electrosurgical device of claim 1, wherein the surface-contact detection device includes a plurality of optical transmitters and a plurality of optical receivers circumferentially disposed within the internal cavity and about the central opening defined through the surface-contact detection device.

11. The electrosurgical device of claim 1, wherein the dielectric structure is removably disposed at least partially within the central opening defined through the surface-contact detection device.

12. An electrosurgical system, comprising:
    an energy applicator adapted to direct energy to tissue;
    an electrosurgical power generating source;
    a surface-contact detection device operably associated with the energy applicator and the electrosurgical power generating source, the surface-contact detection device including:
       a first body element;
       a second body element coupled to the first body element, the second body element defining a central opening through the surface-contact detection device;
       at least one optical transmitter coupled to the first body element and configured to generate optical signals;
       a lens member coupled to the first and second body elements such that an internal cavity is defined between the lens member and the first and second body elements, the lens member disposed laterally offset from the central opening and configured to reflect optical signals generated by the at least one optical transmitter when the lens member is disposed in contact with tissue; and
       at least one optical receiver coupled to the second body element and configured to receive optical signals reflected by the lens member, the at least one optical transmitter and the at least one optical receiver disposed within the internal cavity; and
    a dielectric structure disposed at least partially within the central opening defined through the surface-contact detection device,
    wherein the electrosurgical power generating source is adapted to transmit energy to the energy applicator when it is determined that the lens member is disposed in contact with tissue.

13. The electrosurgical system of claim 12, wherein at least one operating parameter associated with the electrosurgical power generating source is controlled based on an electrical signal received from the surface-contact detection device.

14. The electrosurgical system of claim 13, wherein the electrical signal is generated by the surface-contact detection device in response to a determination that optical signals generated by the at least one optical transmitter result in reflected optical signals received at the at least one optical receiver.

15. The electrosurgical system of claim 13, wherein the at least one operating parameter associated with the electrosurgical power generating source is selected from the group consisting of temperature, impedance, power, current, voltage, mode of operation, and duration of application of electromagnetic energy.

16. The electrosurgical system of claim 12, wherein the dielectric structure extends distally of a distal end of the central opening defined through the surface-contact detection device.

17. A surface-contact detection device for use with an electrosurgical device, the surface-contact detection device comprising:
  a first body element;
  a second body element coupled to the first body element, the second body element defining a central opening through the surface-contact detection device;
  a lens member coupled to the first and second body elements such that an internal cavity is defined between the lens member and the first and second body elements;
  at least one optical transmitter disposed within the internal cavity and coupled to the first body element, the at least one optical transmitter configured to generate optical signals; and
  at least one optical receiver disposed within the internal cavity and coupled to the second body element, the at least one optical receiver configured to receive optical signals reflected by the lens member; and
  a dielectric structure disposed at least partially within the central opening defined through the surface-contact detection device.

18. The surface-contact detection device of claim 17, further including a plurality of optical transmitters and a plurality of optical receivers circumferentially disposed within the internal cavity and about the central opening defined through the surface-contact detection device.

19. The surface-contact detection device of claim 17, wherein the dielectric structure fills the entirety of the central opening defined through the surface-contact detection device.

20. The surface-contact detection device of claim 17, wherein the dielectric structure extends distally of a distal end of the central opening defined through the surface-contact detection device.

* * * * *